US011547431B2

(12) United States Patent
Hibner et al.

(10) Patent No.: US 11,547,431 B2
(45) Date of Patent: Jan. 10, 2023

(54) ULTRASONIC SURGICAL INSTRUMENT WITH REMOVABLE SHAFT ASSEMBLY PORTION

(71) Applicant: Ethicon LLC, Guaynabo, PR (US)

(72) Inventors: John A. Hibner, Mason, OH (US); Thomas B. Remm, Milford, OH (US)

(73) Assignee: Cilag GmbH International, Zug (CH)

( * ) Notice: Subject to any disclaimer, the term of this patent is extended or adjusted under 35 U.S.C. 154(b) by 640 days.

(21) Appl. No.: 16/549,817

(22) Filed: Aug. 23, 2019

(65) Prior Publication Data
US 2020/0078042 A1 Mar. 12, 2020

Related U.S. Application Data

(63) Continuation of application No. 15/270,600, filed on Sep. 20, 2016, now Pat. No. 10,492,820.
(Continued)

(51) Int. Cl.
*A61B 17/32* (2006.01)
*B23P 19/04* (2006.01)
(Continued)

(52) U.S. Cl.
CPC ............ *A61B 17/320092* (2013.01); *A61B 17/320068* (2013.01); *B23P 19/02* (2013.01);
(Continued)

(58) Field of Classification Search
CPC .... A61B 17/320092; A61B 17/320068; A61B 2017/2902; A61B 2017/2931;
(Continued)

(56) References Cited

U.S. PATENT DOCUMENTS 5,322,055 A 6/1994 Davison et al.
5,324,299 A 6/1994 Davison et al.
(Continued)

FOREIGN PATENT DOCUMENTS

CN 1676107 A * 10/2005 ..... A61B 17/320092
CN 1676107 A 10/2005
(Continued)

OTHER PUBLICATIONS

U.S. Appl. No. 16/368,969.
(Continued)

*Primary Examiner* — Bayan Salone
(74) *Attorney, Agent, or Firm* — Frost Brown Todd LLC

(57) ABSTRACT

An apparatus includes a body, a shaft assembly, and an end effector. The shaft assembly includes an outer tube, an inner tube, and an acoustic waveguide. The end effector includes an ultrasonic blade and a clamp arm. The ultrasonic blade is acoustically coupled with the acoustic waveguide. A first portion of the clamp arm is pivotably coupled with a distal end of the outer tube. A second portion of the clamp arm is pivotably coupled with a distal end of the inner tube. The outer tube and the inner tube are configured to removably couple with the body such that the outer tube, the inner tube, and the clamp arm are configured to removably couple with the body and the remainder of the shaft assembly and end effector as a unit.

20 Claims, 34 Drawing Sheets

Related U.S. Application Data

(60) Provisional application No. 62/242,440, filed on Oct. 16, 2015, provisional application No. 62/263,102, filed on Dec. 4, 2015, provisional application No. 62/329,381, filed on Apr. 29, 2016.

(51) Int. Cl.
*B23P 19/02* (2006.01)
*B25B 27/02* (2006.01)
*A61B 17/29* (2006.01)

(52) U.S. Cl.
CPC .............. *B23P 19/04* (2013.01); *B25B 27/02* (2013.01); *A61B 2017/2902* (2013.01); *A61B 2017/2931* (2013.01); *A61B 2017/320071* (2017.08); *A61B 2017/320072* (2013.01); *A61B 2017/320093* (2017.08); *A61B 2017/320094* (2017.08)

(58) Field of Classification Search
CPC ....... A61B 2017/320071; A61B 2017/320072; A61B 2017/320093; A61B 2017/320094; A61B 2017/0023; A61B 2017/0046; A61B 2017/32007; A61B 2017/320075; A61B 2017/320089; A61B 2017/320095; A61B 2017/00526; A61B 2090/031; A61B 2090/0806; B23P 19/02; B23P 19/04; B25B 27/02
See application file for complete search history.

(56) References Cited

U.S. PATENT DOCUMENTS

| | | | |
|---|---|---|---|
| 5,873,873 A | 2/1999 | Smith et al. | |
| 5,897,523 A | 4/1999 | Wright et al. | |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright et al. | |
| 6,165,191 A | 12/2000 | Shibata et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,454,782 B1 | 9/2002 | Schwemberger | |
| 6,458,142 B1 | 10/2002 | Faller et al. | |
| 6,500,176 B1 | 12/2002 | Truckai et al. | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 6,887,252 B1 | 5/2005 | Okada et al. | |
| 7,052,506 B2 | 5/2006 | Young et al. | |
| 7,112,201 B2 * | 9/2006 | Truckai | A61B 18/1442 |
| 7,125,409 B2 | 10/2006 | Truckai et al. | |
| 7,135,030 B2 | 11/2006 | Schwemberger et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,544,200 B2 | 6/2009 | Houser | |
| 7,621,930 B2 | 11/2009 | Houser | |
| 8,057,498 B2 | 11/2011 | Robertson | |
| 8,142,461 B2 | 3/2012 | Houser et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,107,690 B2 | 8/2015 | Bales, Jr. et al. | |
| 9,308,009 B2 * | 4/2016 | Madan | G16H 40/63 |
| 10,034,685 B2 * | 7/2018 | Boudreaux | A61N 7/00 |
| 10,050,453 B2 | 8/2018 | Miller et al. | |
| 10,172,684 B2 | 1/2019 | Conlon et al. | |
| 10,327,797 B2 | 6/2019 | Conlon et al. | |
| 10,492,820 B2 | 12/2019 | Hibner et al. | |
| 2004/0097911 A1 | 5/2004 | Murakami et al. | |
| 2006/0079874 A1 * | 4/2006 | Faller | A61B 17/32009 |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2008/0234708 A1 | 9/2008 | Houser et al. | |
| 2010/0063528 A1 | 3/2010 | Beaupre | |
| 2012/0112687 A1 | 5/2012 | Houser et al. | |
| 2012/0116265 A1 | 5/2012 | Houser et al. | |
| 2014/0005701 A1 | 1/2014 | Olson et al. | |
| 2014/0005703 A1 | 1/2014 | Stulen et al. | |
| 2014/0151079 A1 | 6/2014 | Furui et al. | |
| 2015/0080924 A1 | 3/2015 | Stulen et al. | |
| 2015/0141981 A1 | 5/2015 | Price et al. | |
| 2015/0148832 A1 | 5/2015 | Boudreaux et al. | |
| 2015/0164532 A1 | 6/2015 | Faller et al. | |
| 2015/0245850 A1 | 9/2015 | Hibner et al. | |
| 2016/0015419 A1 | 1/2016 | Hibner et al. | |
| 2019/0290319 A1 | 9/2019 | Conlon et al. | |

FOREIGN PATENT DOCUMENTS

| | | | | |
|---|---|---|---|---|
| CN | 101141922 A | | 3/2008 | |
| CN | 101141922 A | * | 3/2008 | ..... A61B 17/320092 |
| CN | 103052362 A | * | 4/2013 | ..... A61B 17/320092 |
| CN | 103052362 A | | 4/2013 | |
| CN | 103313672 A | | 9/2013 | |
| CN | 103313672 A | * | 9/2013 | ....... A61B 17/00234 |
| CN | 103315807 A | | 9/2013 | |
| CN | 103442658 A | | 12/2013 | |
| CN | 103442658 A | * | 12/2013 | ....... A61B 17/00234 |
| CN | 103703651 A | | 4/2014 | |
| EP | 2042112 A2 | | 4/2009 | |
| EP | 2510891 A1 | | 10/2012 | |
| EP | 2641552 A2 | | 9/2013 | |
| EP | 2692297 A2 | | 2/2014 | |
| EP | 2992842 A1 | | 3/2016 | |
| JP | 2002-200094 A | | 7/2002 | |
| JP | 2002200094 A | * | 7/2002 | |
| JP | 2004-154256 A | | 6/2004 | |
| JP | 2004154256 A | * | 6/2004 | |
| JP | 2005-278934 A | | 10/2005 | |
| JP | 2005278934 A | * | 10/2005 | ..... A61B 17/320092 |
| JP | 2010-167084 A | | 8/2010 | |
| JP | 2010167084 A | * | 8/2010 | |
| JP | 2013-545535 A | | 12/2013 | |
| WO | WO 2000/078237 A1 | | 12/2000 | |
| WO | WO 2010/150618 A1 | | 12/2010 | |
| WO | WO 2016/036656 A1 | | 3/2016 | |

OTHER PUBLICATIONS

Brazilian Search Report dated Jun. 16, 2020 for Application No. BR 112018007524-8, 4 pgs.
Brazilian Search Report dated Jun. 16, 2020 for Application No. BR 112018007533-7, 4 pgs.
Chinese Office Action, The Second Office Action, dated Jun. 17, 2020 for Application No. CN 201780002074.0, 5 pgs.
Chinese Office Action, The First Office Action, and First Search, dated Dec. 11, 2019 for Application No. CN 201680035752.9, 17 pgs.
Chinese Office Action, The Second Office Action dated Jun. 12, 2020 for Application No. CN 201680035752.9, 5 pgs.
Chinese Office Action, The Third Office Action dated Oct. 23, 2020 for Application No. CN 201680035752.9, 7 pgs.
Chinese Office Action, Notification of the First Office Action, and First Search, dated Dec. 25, 2019 for Application No. CN 201680035754.8, 15 pgs.

(56) References Cited

OTHER PUBLICATIONS

Chinese Office Action, Notification of the Second Office Action, dated Sep. 9, 2020 for Application No. CN 201680035754.8, 7 pgs.
European Search Report, Extended, and Written Opinion dated Oct. 22, 2020 for Application No. EP 20185283.7, 10 pgs.
Japanese Office Action, Notice of Reasons for Refusal, dated Mar. 2, 2021 for Application No. JP 2018-556369, 7 pgs.
Japanese Office Action, Notice of Reasons for Refusal, and First Search, dated Oct. 27, 2020 for Application No. JP 2018-519283, 32 pgs.
Japanese Office Action, Notice of Reasons for Refusal, and First Search, dated Nov. 24, 2020 for Application No. JP 2018-519287, 25 pgs.
Chinese Search Report dated Sep. 6, 2019 for Application No. 201780002074.0, 1 page.
Chinese Office Action dated Sep. 19, 2019 for Application No. 201780002074.0, 12 pages.
International Search Report and Written Opinion dated Jan. 25, 2017 for International Application No. PCT/US2016/055923, 11 pages.
International Search Report and Written Opinion dated Mar. 8, 2017 for International Application No. PCT/US2016/055926, 18 pages.
International Search Report and Written Opinion dated Aug. 22, 2017 for International Application No. PCT/US2017/029274, 15 pages.
U.S. Appl. No. 61/410,603, filed Nov. 5, 2010.
U.S. Appl. No. 62/242,440, filed Oct. 16, 2015.
U.S. Appl. No. 62/263,102, filed Dec. 4, 2015.
U.S. Appl. No. 62/329,381, filed Apr. 29, 2016.
U.S. Appl. No. 14/258,179, filed Apr. 22, 2014.

* cited by examiner

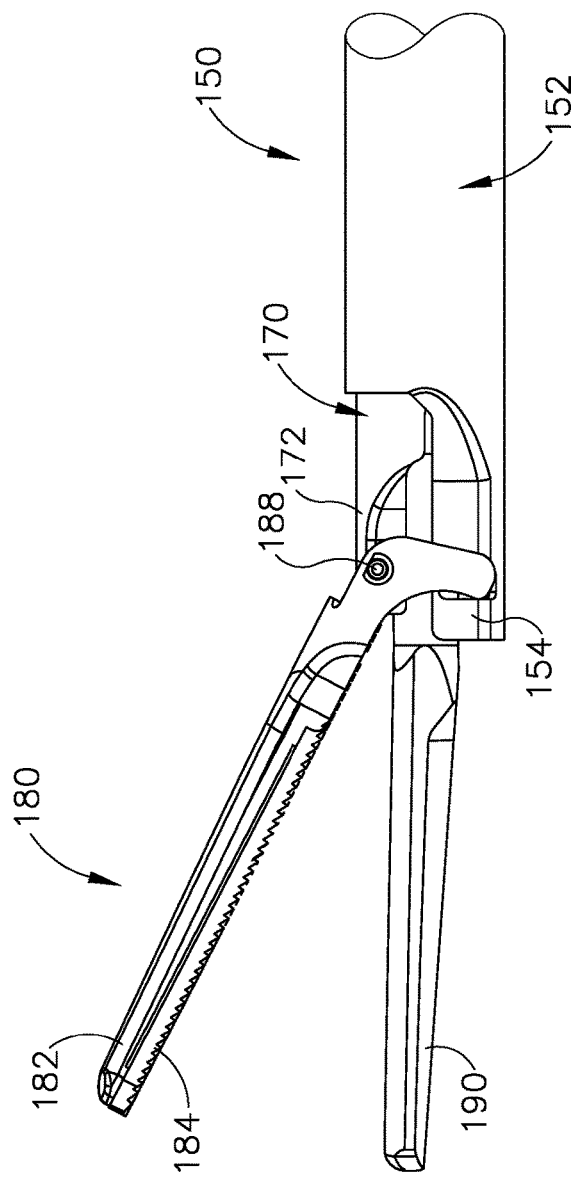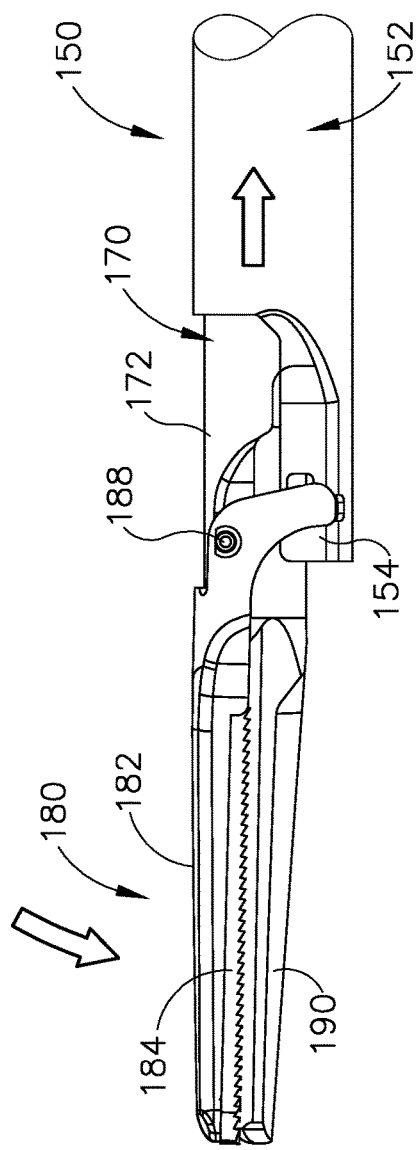

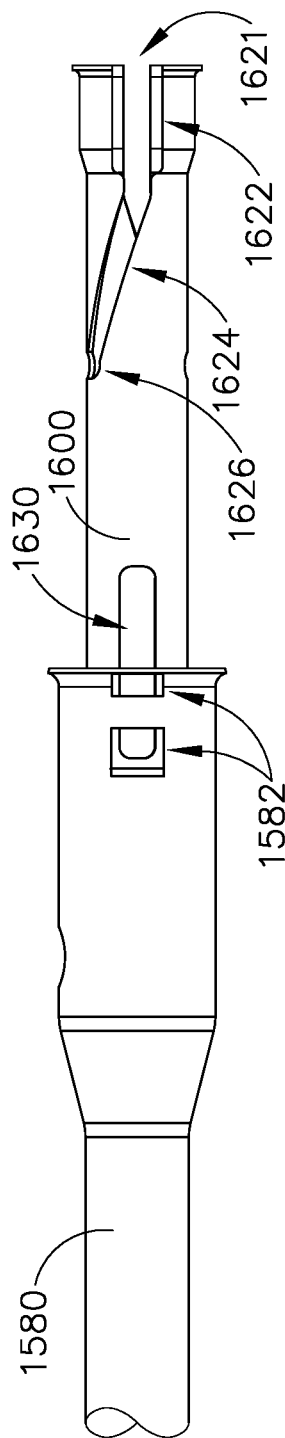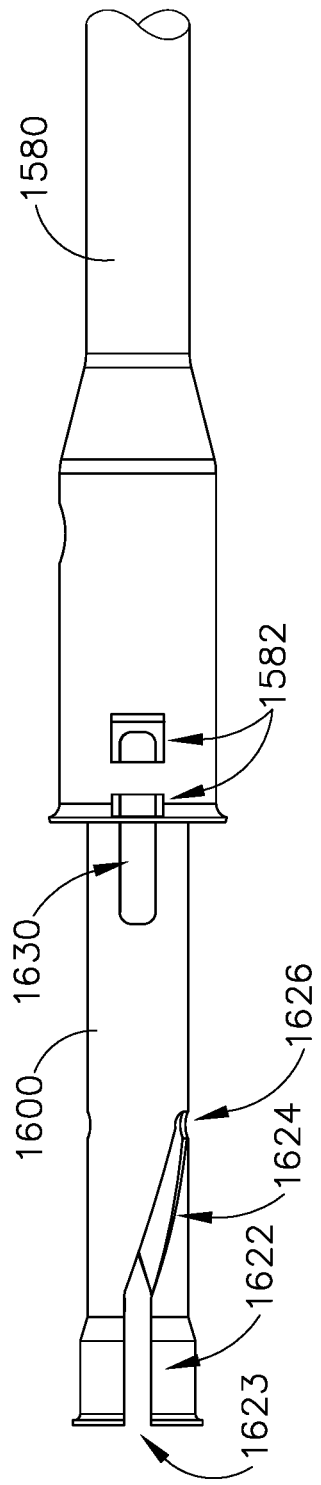
Fig. 18D
Fig. 18E

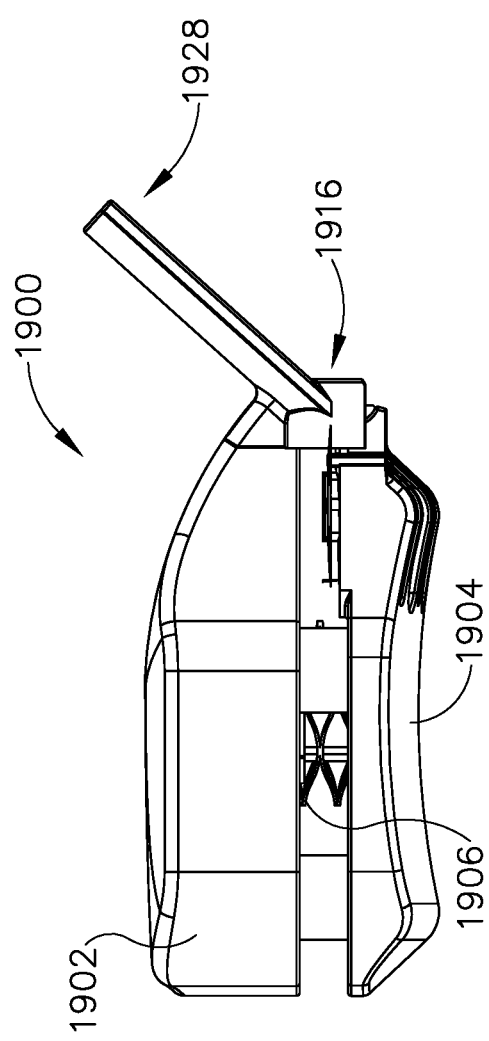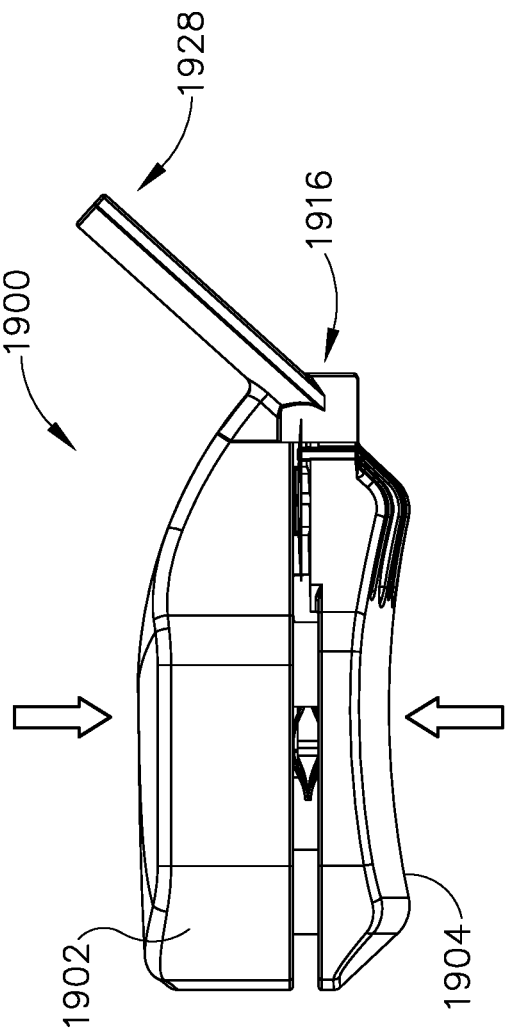

ULTRASONIC SURGICAL INSTRUMENT WITH REMOVABLE SHAFT ASSEMBLY PORTION

PRIORITY

This application is a continuation of U.S. patent application Ser. No. 15/270,600, entitled "Ultrasonic Surgical Instrument with Removable Shaft Assembly Portion," filed Sep. 20, 2016, published as U.S. Pub. No. 2017/0105751 on Apr. 20, 2017, issued as U.S. Pat. No. 10,492,820 on Dec. 3, 2019.

U.S. patent application Ser. No. 15/270,600, issued as U.S. Pat. No. 10,492,820 on Dec. 3, 2019, claims priority to U.S. Provisional Pat. App. No. 62/242,440, entitled "Ultrasonic Surgical Instrument with Disposable Outer Tube," filed Oct. 16, 2015, the disclosure of which is incorporated by reference herein.

U.S. patent application Ser. No. 15/270,600, issued as U.S. Pat. No. 10,492,820 on Dec. 3, 2019, also claims priority to U.S. Provisional Pat. App. No. 62/263,102, entitled "Ultrasonic Surgical Instrument with Disposable Tube Assembly and Clamp Pad," filed Dec. 4, 2015, the disclosure of which is incorporated by reference herein.

U.S. patent application Ser. No. 15/270,600, issued as U.S. Pat. No. 10,492,820 on Dec. 3, 2019, also claims priority to U.S. Provisional Pat. App. No. 62/329,381, entitled "Apparatus to Provide Reusability of Ultrasonic Surgical Instrument Feature," filed Apr. 29, 2016, the disclosure of which is incorporated by reference herein.

BACKGROUND

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008 now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012 now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," issued as U.S. Pat. No. 9,393,037 on Jul. 19, 2016, the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. Pat. App. No. 62/176,880, entitled "Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6A depicts a side elevational view of the end effector of FIG. 4, in the open configuration;

FIG. 6B depicts a side elevational view of the end effector of FIG. 4, in a closed configuration;

FIG. 18D depicts a side view of the proximal ends of the inner tube and outer tube of the first disposable sub-assembly of FIG. 11;

FIG. 18E depicts a side view, opposite of that of FIG. 18D, of the proximal ends of the inner tube and outer tube of the first disposable sub-assembly of FIG. 11;

FIG. 28A depicts a side view of the clamp pad loader assembly of FIG. 27, shown in a first position for receiving a clamp arm within the clamp pad loader assembly;

FIG. 28B depicts a side view of the clamp pad loader assembly of FIG. 27, shown in a second position for loading the clamp pad onto an inserted clamp arm;

Figure 1:
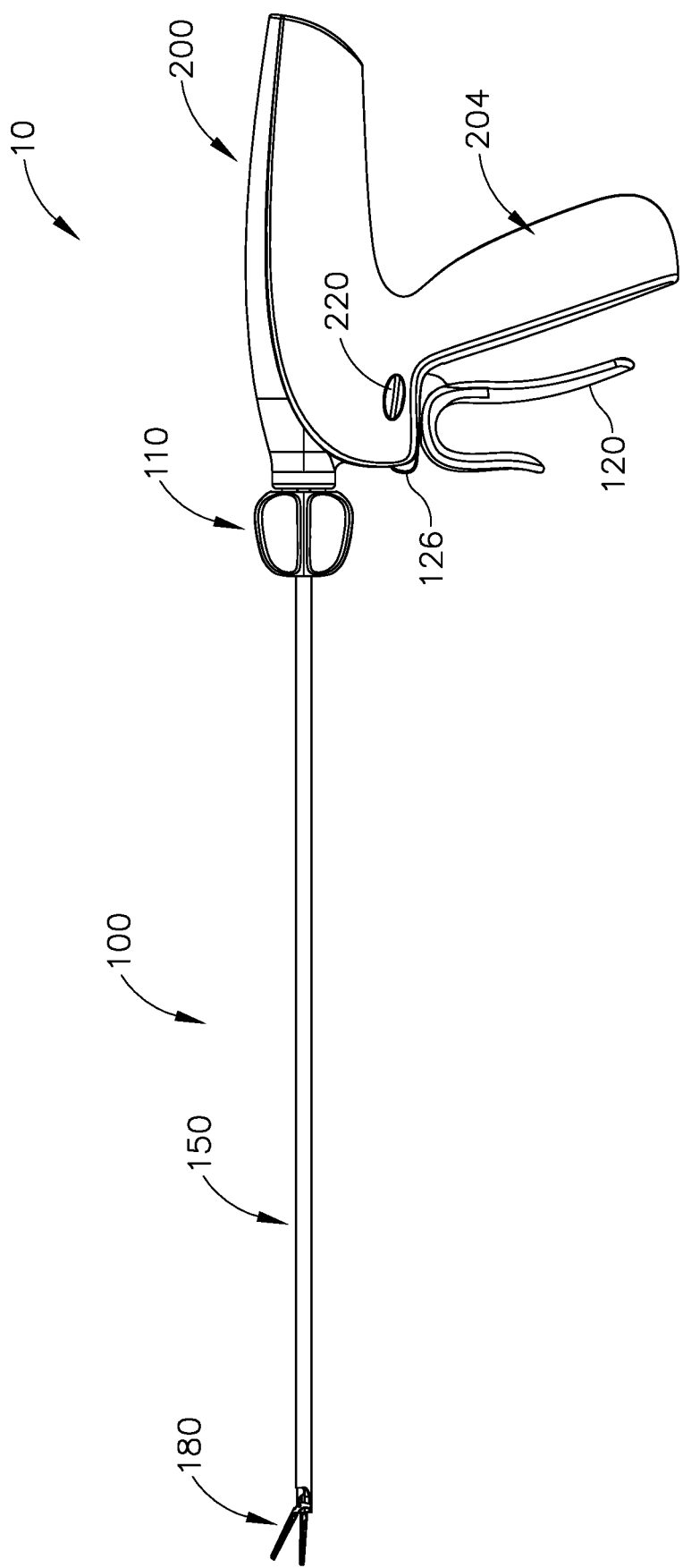
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Overview of Exemplary Ultrasonic Surgical Instrument

Figure 2:
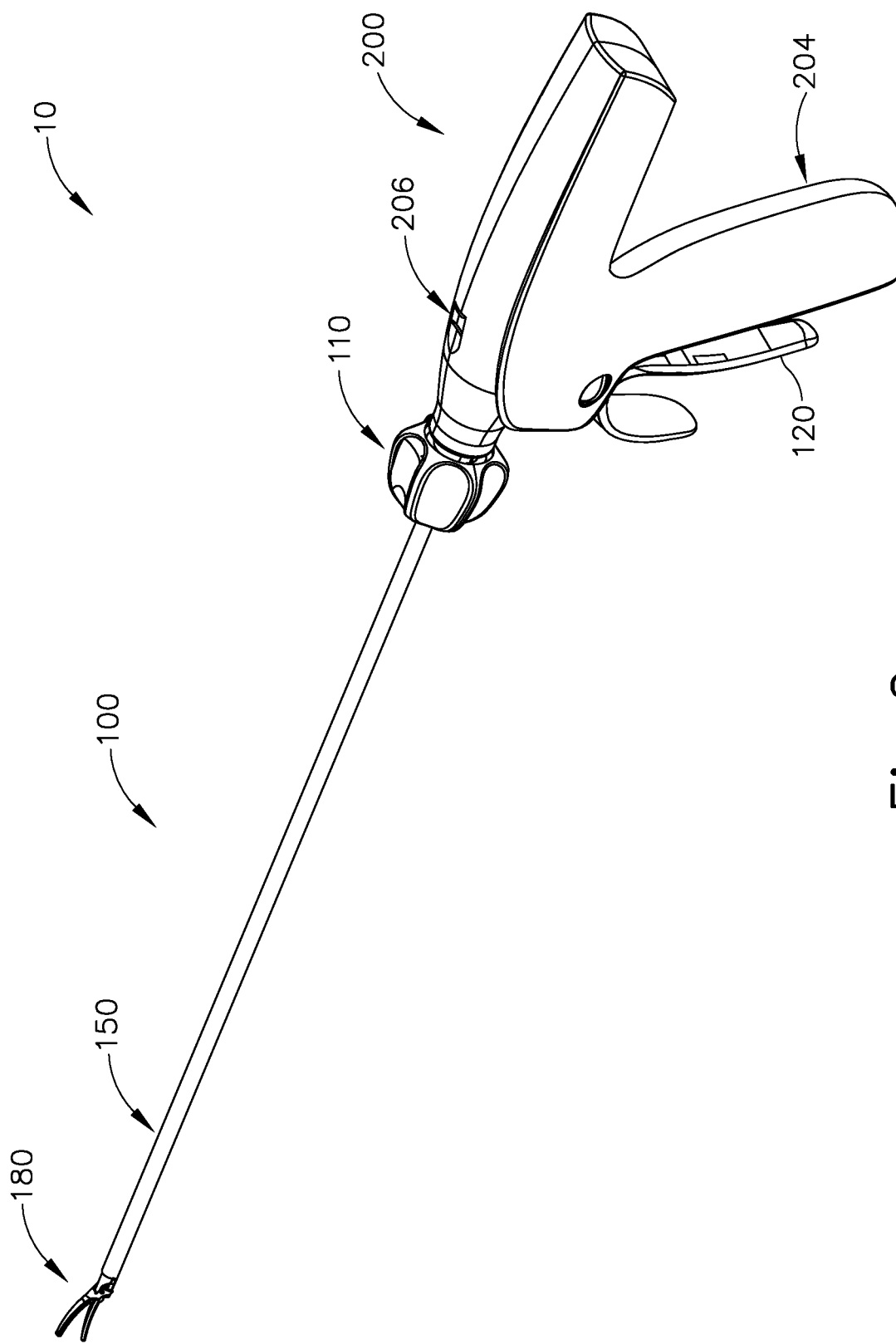
FIG. 2 depicts a perspective view of the instrument of FIG. 1.
Figure 3:
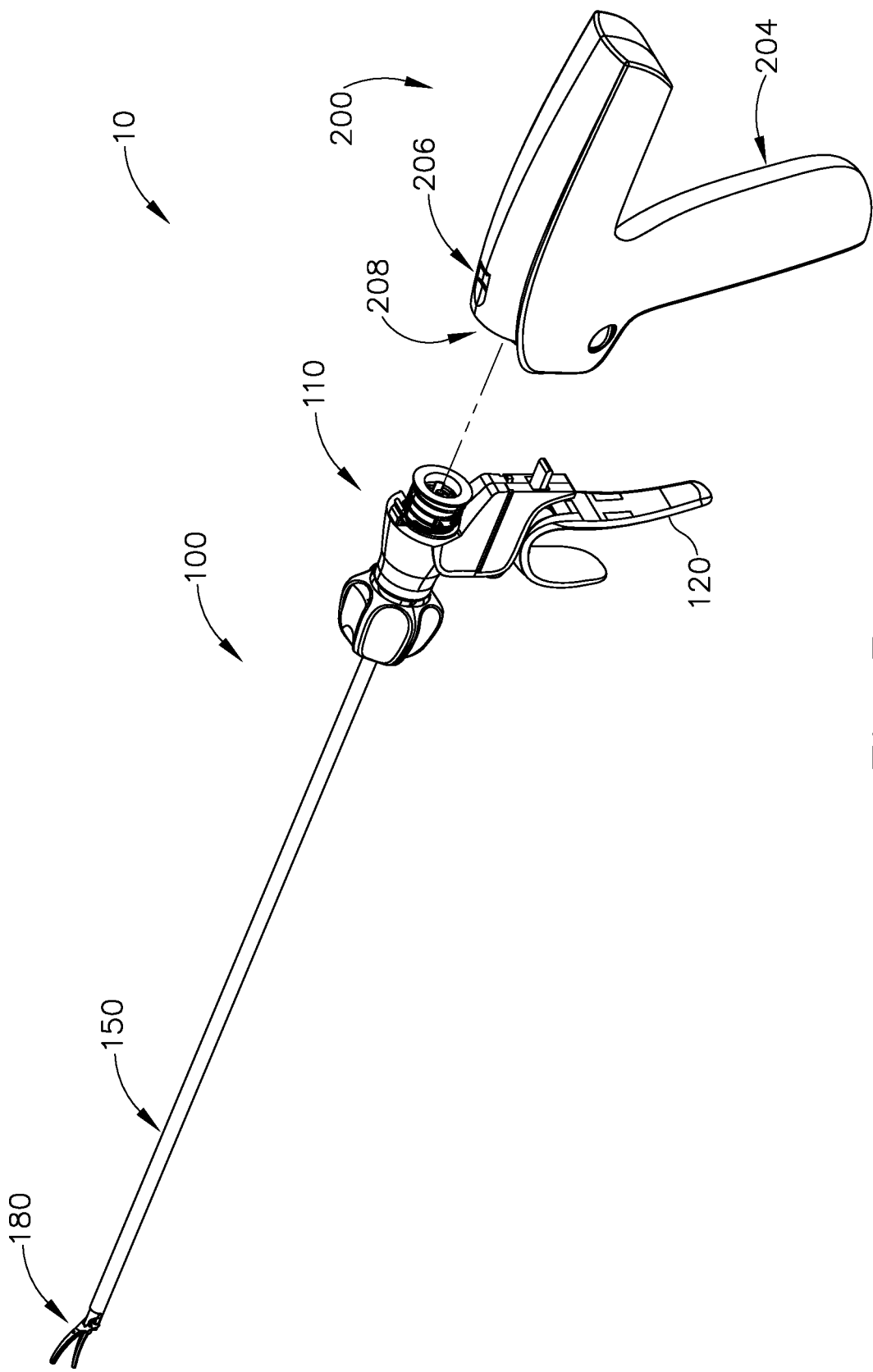
FIG. 3 depicts a perspective view of the instrument of FIG. 1, with a disposable portion separated from a reusable portion.
Figure 4:
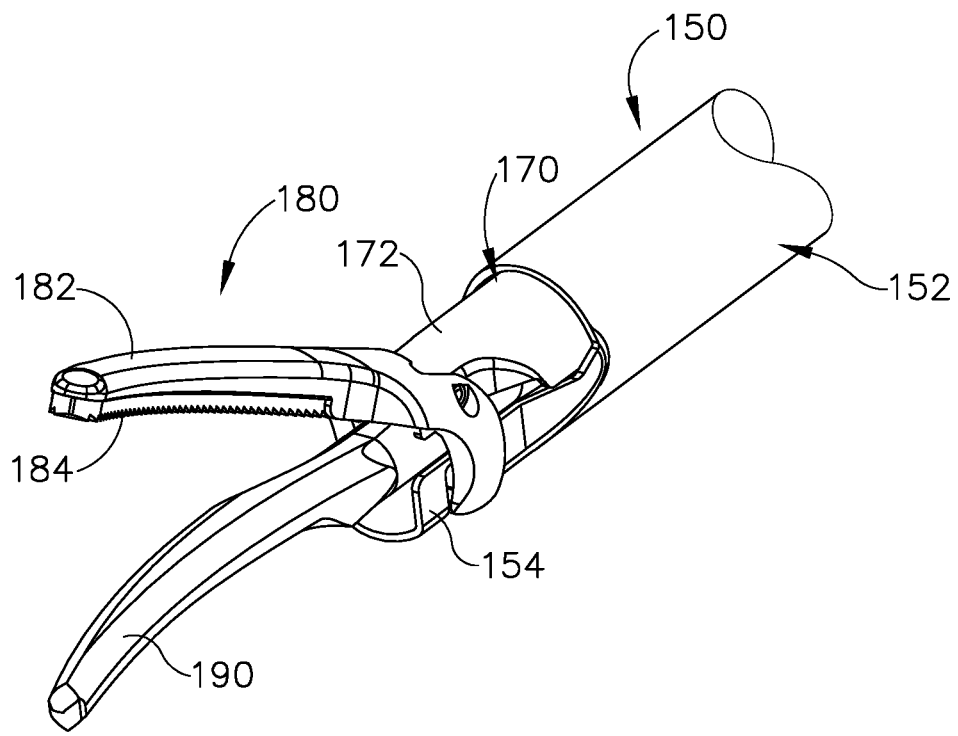
FIG. 4 depicts a perspective view of an end effector of the instrument of FIG. 1, in an open configuration.

FIGS. 1-3 show an exemplary ultrasonic surgical instrument (10) that is configured to be used in minimally invasive surgical procedures (e.g., via a trocar or other small diameter access port, etc.). As will be described in greater detail below, instrument (10) is operable to cut tissue and seal or weld tissue (e.g., a blood vessel, etc.) substantially simultaneously. Instrument (10) of this example comprises a disposable assembly (100) and a reusable assembly (200). The distal portion of reusable assembly (200) is configured to removably receive the proximal portion of disposable assembly (100), as seen in FIGS. 2-3, to form instrument (10).

In an exemplary use, assemblies (100, 200) are coupled together to form instrument (10) before a surgical procedure, the assembled instrument (10) is used to perform the surgical procedure, and then assemblies (100, 200) are decoupled from each other for further processing. In some instances, after the surgical procedure is complete, disposable assembly (100) is immediately disposed of while reusable assembly (200) is sterilized and otherwise processed for re-use. By way of example only, reusable assembly (200) may be sterilized in a conventional relatively low temperature, relatively low pressure, hydrogen peroxide sterilization process. Alternatively, reusable assembly (200) may be sterilized using any other suitable systems and techniques (e.g., autoclave, etc.). In some versions, reusable assembly (200) may be sterilized and reused approximately 100 times. Alternatively, reusable assembly (200) may be subject to any other suitable life cycle. For instance, reusable assembly (200) may be disposed of after a single use, if desired. While disposable assembly (100) is referred to herein as being "disposable," it should be understood that, in some instances, disposable assembly (100) may also be sterilized and otherwise processed for re-use. By way of example only, disposable assembly (100) may be sterilized and reused approximately 2-30 times, using any suitable systems and techniques. Alternatively, disposable assembly (100) may be subject to any other suitable life cycle.

In some versions, disposable assembly (100) and/or reusable assembly (200) includes one or more features that are operable to track usage of the corresponding assembly (100, 200), and selectively restrict operability of the corresponding assembly (100, 200) based on use. For instance, disposable assembly (100) and/or reusable assembly (200) may include one or more counting sensors and a control logic (e.g., microprocessor, etc.) that is in communication with the counting sensor(s). The counting sensor(s) may be able to detect the number of times the ultrasonic transducer of instrument (10) is activated, the number of surgical procedures the corresponding assembly (100, 200) is used in, the number of trigger closures, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (100, 200). In instances where the control logic stores two or more threshold values (e.g., a first threshold for number of activations and a second threshold for number of surgical procedures, etc.), the control logic may disable operability of one or more components in the corresponding assembly (100, 200) the first time one of those thresholds is exceeded, or on some other basis.

In versions where a control logic is operable to disable instrument (10) based on the amount of use, the control logic may also determine whether instrument (10) is currently being used in a surgical procedure, and refrain from disabling instrument (10) until that particular surgical procedure is complete. In other words, the control logic may allow the operator to complete the current surgical procedure but prevent instrument (10) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (10) will be apparent to those of ordinary skill in the art in view of the teachings herein. Of course, some versions of instrument (10) may simply omit features that track and/or restrict the amount of usage of instrument (10).

Figure 7:
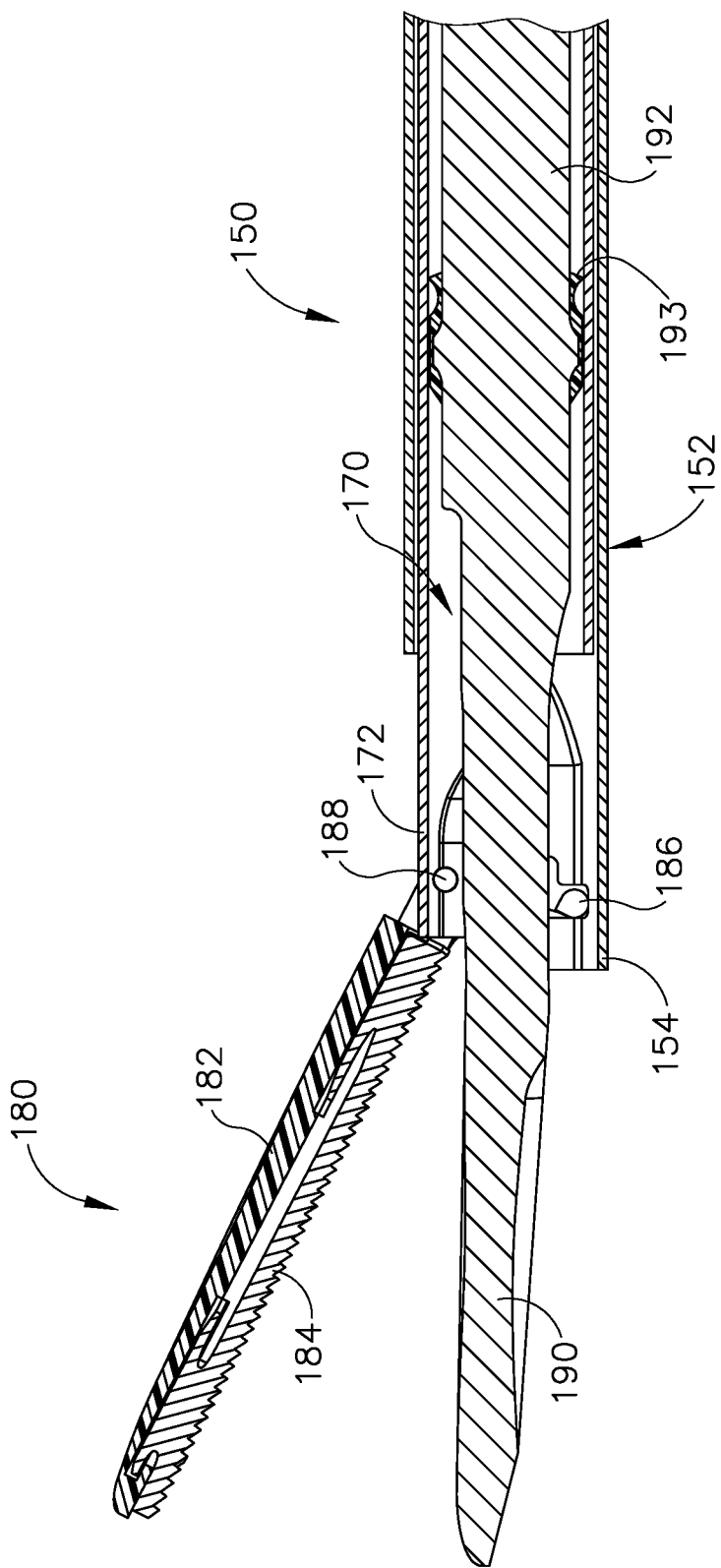
FIG. 7 depicts a side cross-sectional view of the end effector of FIG. 4, in the open configuration.
Figure 8:
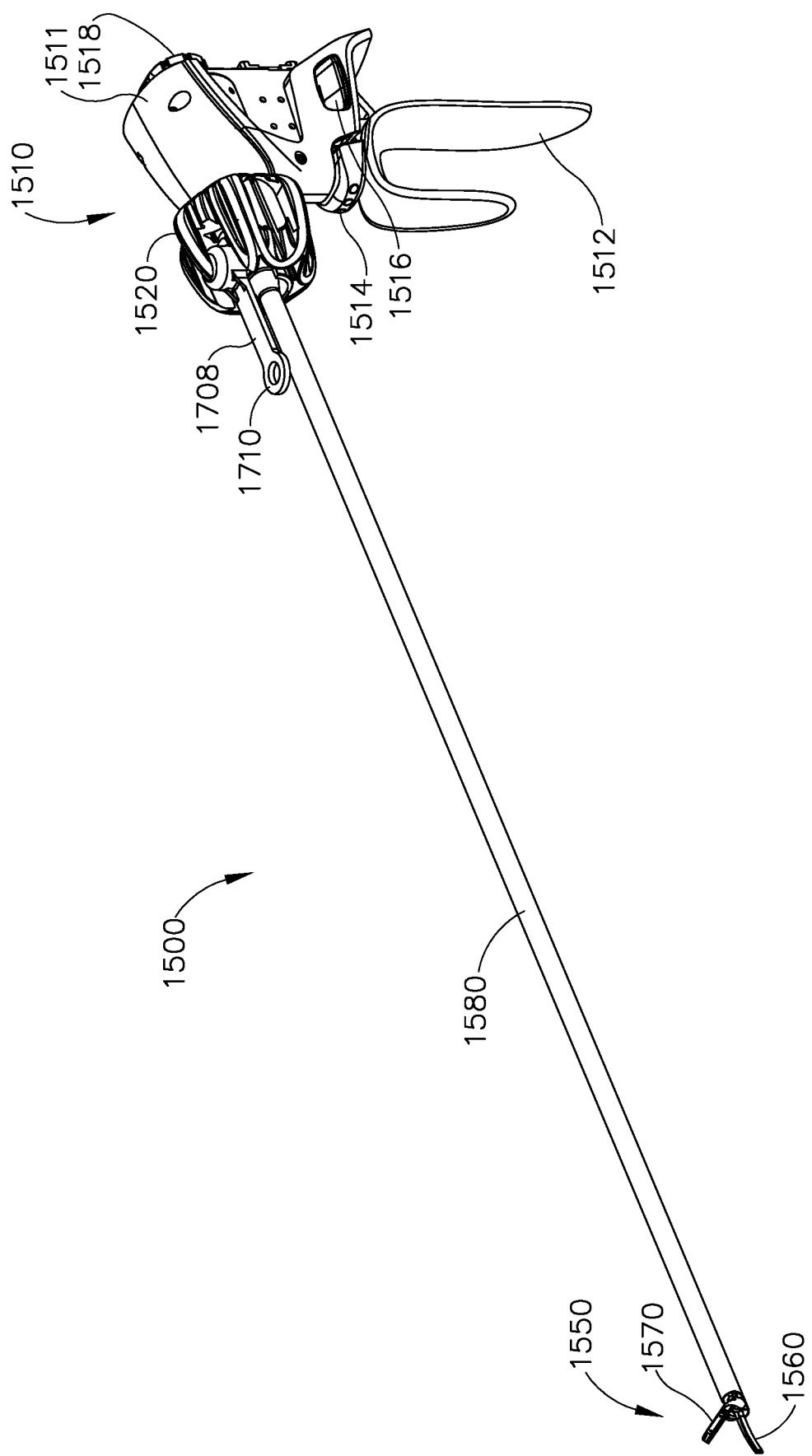
FIG. 8 depicts a perspective view of another exemplary alternative disposable portion of an ultrasonic surgical instrument that may be used with a variation of the reusable portion of the instrument of FIG. 1.
Figure 9:
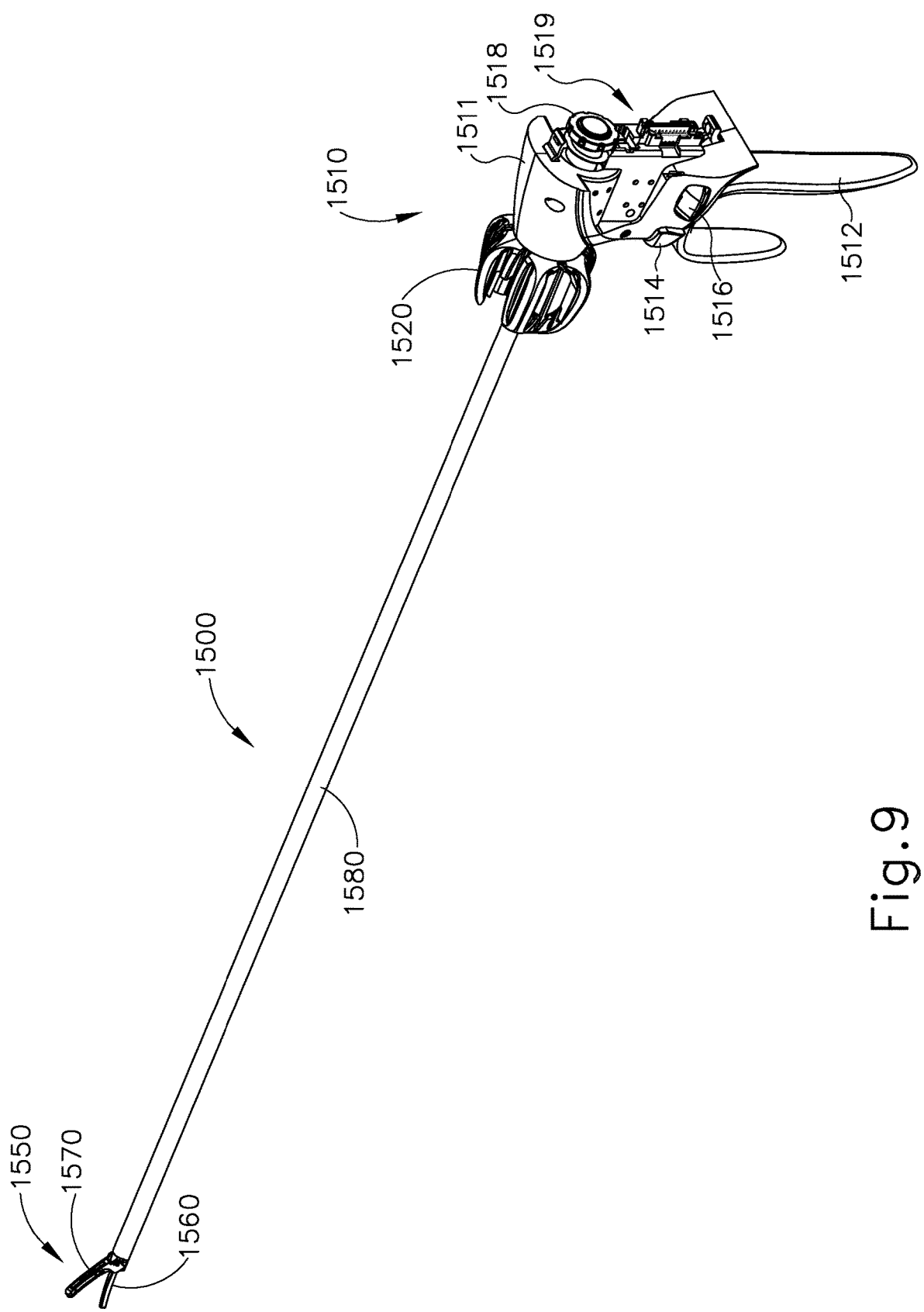
FIG. 9 depicts another perspective view of the disposable portion of FIG. 8.

Disposable assembly (100) of the present example comprises a body portion (110), a shaft assembly (150) extending distally from body portion (110), and an end effector (180) located at the distal end of shaft assembly (150). As best seen in FIGS. 4-7, end effector (180) of this example comprises a clamp arm (182) and an ultrasonic blade (190). Clamp arm (182) includes a clamp pad (184), which faces blade (190). As shown in FIGS. 6A-6B and as will be described in greater detail below, clamp arm (182) is pivotable toward and away from blade (190) to selectively compress tissue between clamp pad (184) and blade (190). As seen in FIG. 7, blade (190) is an integral feature of the distal end of an acoustic waveguide (192), which extends coaxially through tubes (152, 170), and which is configured to communicate ultrasonic vibrations to blade (190) as will be described in greater detail below.

Figure 5:
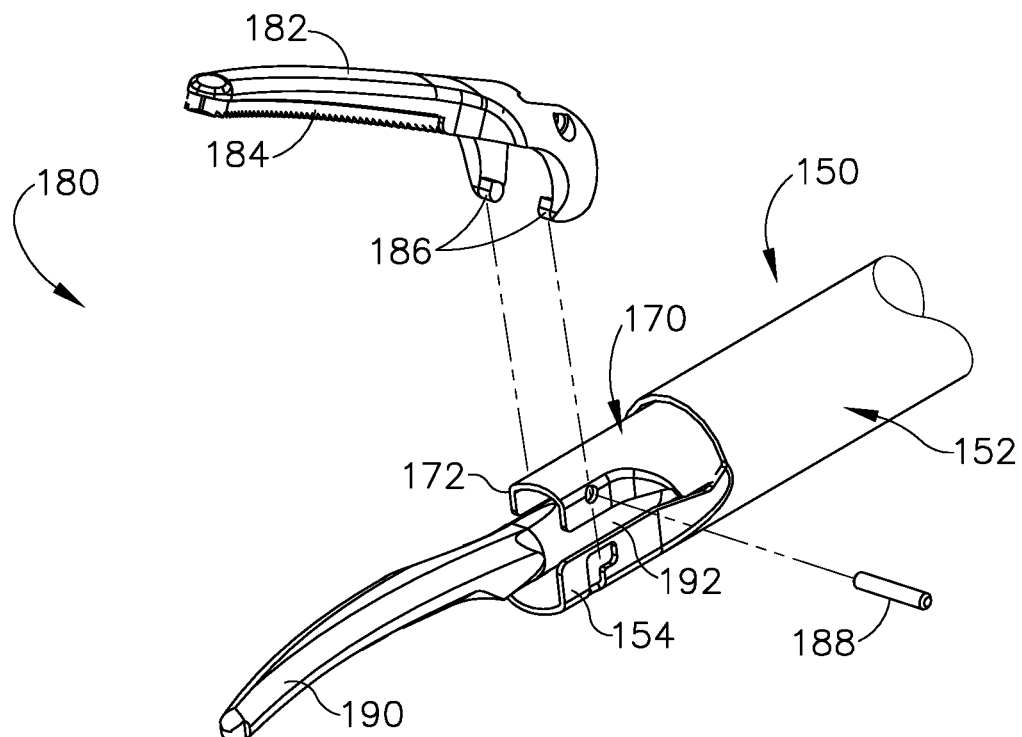
FIG. 5 depicts a partially exploded view of the end effector of FIG. 4.

Shaft assembly (150) comprises an outer tube (152) and an inner tube (170). Outer tube (152) is operable to translate longitudinally relative to inner tube (170) to selectively pivot clamp arm (182) toward and away from blade (190). To accomplish this, and as best seen in FIGS. 5 and 7, integral pin features (186) of clamp arm (182) pivotally secure a first portion of clamp arm (182) to a distally projecting tongue (154) of outer tube (152); while an inserted pin (188) pivotally secures a second portion of clamp arm (182) to a distally projecting tongue (172) of inner tube (170). Thus, as can be seen in the transition from FIG. 6A to FIG. 6B, tubes (152, 170) cooperate to pivot clamp arm (182) toward blade (190) when outer tube (152) is retracted proximally relative to inner tube (170). It should be understood that clamp arm (182) may be pivoted back away from blade (190) (e.g., from the position shown in FIG. 6B to the position shown in FIG. 6A) by translating outer tube (152) distally relative to inner tube (170), in reverse of the operation shown in FIGS. 6A-6B. In an exemplary use, clamp arm (182) may be pivoted toward blade (190) to grasp, compress, seal, and sever tissue captured between clamp pad (184) and blade (190). Clamp arm (182) may be pivoted away from blade (190) to release tissue from between clamp pad (184) and blade (190); and/or to perform blunt dissection of tissue engaging opposing outer surfaces of clamp arm (182) and blade (190).

Reusable assembly (200) comprises various features that are operable to activate blade, including a battery and an ultrasonic transducer. Reusable assembly (200) further includes features that are operable to couple the ultrasonic transducer with waveguide to thereby couple the ultrasonic transducer with blade (190). In the present example, the distal end of blade (190) is located at a position corresponding to an anti-node associated with resonant ultrasonic vibrations communicated through waveguide (192), in order to tune the acoustic assembly to a preferred resonant frequency $f_o$ when the acoustic assembly is not loaded by tissue. When the transducer assembly is energized, the distal end of blade (190) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When the transducer assembly of the present example is activated, these mechanical oscillations are transmitted through waveguide (192) to reach blade (190), thereby providing oscillation of blade (190) at the resonant ultrasonic frequency. Thus, when tissue is secured between blade (190) and clamp pad (184), the ultrasonic oscillation of blade (190) may simultaneously sever the tissue and denature the proteins in adjacent tissue cells, thereby providing a coagulative effect with relatively little thermal spread. In some versions, an electrical current may also be provided through blade (190) and/or clamp pad (184) to also seal the tissue.

In addition to the foregoing, disposable assembly (100) and/or reusable assembly (200) may be constructed and operable in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. In addition, or in the alternative, disposable assembly (100) and/or reusable assembly (200) may be constructed and operable in accordance with at least some of the teachings of U.S. Pub. No. 2016/0015419, entitled "Ultrasonic Surgical Instrument with Removable Handle Assembly," published Jan. 21, 2016, issued as U.S. Pat. No. 10,349,967 on Jul. 16, 2019, the disclosure of which is incorporated by reference herein. Other suitable components, features, and operabilities that may be incorporated into disposable assembly (100) and/or reusable assembly (200) and variations thereof will be apparent to those of ordinary skill in the art in view of the teachings herein.

II. Further Exemplary Alternative Disposable Assembly for Ultrasonic Surgical Instrument with Removable Acoustic Waveguide FIGS. 8-11 show another exemplary alternative disposable assembly (1500) that may be used with a variation of reusable assembly (200). To the extent that the following discussion omits various details of disposable assembly (1500), it should be understood that disposable assembly (1500) may incorporate the various details described above and/or details described in any of the various references that are cited herein. Other suitable details will be apparent to those of ordinary skill in the art in view of the teachings herein.

Disposable assembly (1500) of the present example comprises a first disposable sub-assembly (1502) and a second disposable sub-assembly (1504). A disposable clamp pad (1800) connects with and is separable from components of first disposable sub-assembly (1502) as will be described further below. Sub-assemblies (1502, 1504) are configured to be coupled together in order to form disposable assembly (1500), which may then be coupled with a variation of reusable assembly (200) to form a complete ultrasonic surgical instrument. After the ultrasonic surgical instrument is used in a surgical procedure, disposable assembly (1500) may be removed from the variation of reusable assembly (200); and then first disposable sub-assembly (1502) may be removed from second disposable sub-assembly (1504). In some such instances, the variation of reusable assembly (200) may be cleaned, sterilized, and re-used up to 100 times (by way of example only). First disposable sub-assembly (1502) may be cleaned, sterilized, and re-used up to 5 times (by way of example only). Clamp pad (1800) may be disposed of, such that clamp pad (1800) is only used one single time. Second disposable sub-assembly (1504) may be cleaned, sterilized, and re-used between 5 to 10 times (by way of example only). Still in some other versions, clamp pad (1800) may be non-removable and flush port (1700), as will be discussed in greater detail below, may be omitted such that first disposable sub-assembly (1502) is used only one time. Of course, these re-use scenarios are merely illustrative examples. It should nevertheless be understood that the configuration of disposable assembly (1500) may minimize the amount of single-use material that is disposed of after each surgical procedure. This may reduce cost and overall waste as compared to conventional instrumentation.

A. Exemplary First Disposable Sub-Assembly and Clamp Pad

As shown in FIGS. 8-12, first disposable sub-assembly (1502) of the present example comprises an outer tube (1580), a clamp arm (1570), and an inner tube member (1600). Clamp arm (1570) is configured to form an end effector (1550) with an ultrasonic blade (1560), which is part of second disposable sub-assembly (1504) as will be described in greater detail below. Clamp arm (1570) is pivotably coupled with outer tube (1580) and with inner tube member (1600). Outer tube (1580) is configured to translate longitudinally while inner tube member (1600) remains stationary, which drives clamp arm (1570) to pivot between an open position (FIG. 10A) and a closed position (FIG. 10B). In the closed position, clamp arm (1570) is operable to clamp tissue against blade (1560), which may then be ultrasonically activated to sever and/or seal the tissue as described herein and in various references cited herein.

As shown in FIGS. 12-15B, clamp arm (1570) of the present example comprises a pair of pin openings (1572) and a pair of pivot studs (1576). Pin openings (1572) are configured to receive a pin (1610), which is also disposed in a pin opening (1602) of inner tube member (1600). Pivot studs (1576) are received in openings (1586) of outer tube (1580). Clamp arm (1570) is pivotable about axes defined by pivot studs (1576) and by pin (1610), which enables clamp arm (1570) to transition between the open position (FIG. 10A) and the closed position (FIG. 10B) in response to translation of outer tube (1580) relative to inner tube member (1600).

As shown in FIGS. 12-15B, clamp pad (1800) is removably connected with clamp arm (1570) such that clamp pad (1800) may be replaced. Clamp pad (1800) of the present example comprises polytetrafluoroethylene (PTFE) and includes surface features (e.g., teeth or ridges, etc.) that are configured to promote gripping of tissue. Various suitable materials and configurations that may be used to form clamp pad (1800) will be apparent to those of ordinary skill in the art in view of the teachings herein.

Clamp arm (1570) comprises tension wire (1578) that extends generally longitudinally along clamp arm (1570). Clamp arm (1570) further comprises opening (1579). Tension wire (1578) is positioned within opening (1579) of clamp arm (1570). Clamp pad (1800) is selectively received within opening (1579) from an underside of clamp arm (1570) as shown by the up/down arrows in FIGS. 15A and 15B.

Multiple cooperating features between clamp arm (1570) and clamp pad (1800) provide secure yet removable connection between clamp arm (1570) and clamp pad (1800). First, clamp pad (1800) comprises a groove (1802) configured to receive tension wire (1578) of clamp arm (1570). Second, clamp pad (1800) comprises a pair of studs (1804) on each side of clamp pad (1800) that are configured to engage with corresponding grooves (1574) in clamp arm (1570) to ensure appropriate longitudinal alignment and positioning of clamp pad (1800) relative to clamp arm (1570). In the present example, clamp pad (1800) comprises a boss (1806) projecting upwardly from the remainder of clamp pad (1800), and boss (1806) contains groove (1802) and grooves (1804). Boss (1806) also comprises chamfer (1808) that contacts tension wire (1578) during loading and unloading of clamp pad (1800) within clamp arm (1570). For instance, during the process of loading clamp pad (1800), tension wire (1578) is deflected laterally in a resilient fashion such that clamp pad (1800) can be seated within opening (1579). Once clamp pad (1800) is fully seated within opening (1579), chamfer (1808) is above tension wire (1578) and tension wire (1578) is located within groove (1802). Similarly, when removing or unloading clamp pad (1800) from clamp arm (1570), chamfer (1808) again deflects tension wire (1578) laterally and out from groove (1802). While tension wire (1578) is used to removably secure clamp pad (1800) to clamp arm (1570) in the present example, it should be understood that various other kinds of deformable members may be used to removably secure clamp pad (1800) to clamp arm (1570).

At a proximal end of clamp arm (1570) and clamp pad (1800) are additional cooperating features. Clamp arm (1570) comprises a pair of projections (1573) and clamp pad (1800) comprises a pair of slots (1810) whereby projections (1573) are configured to be received within respective slots (1810) when clamp pad (1800) is installed on clamp arm (1570).

Figure 12:
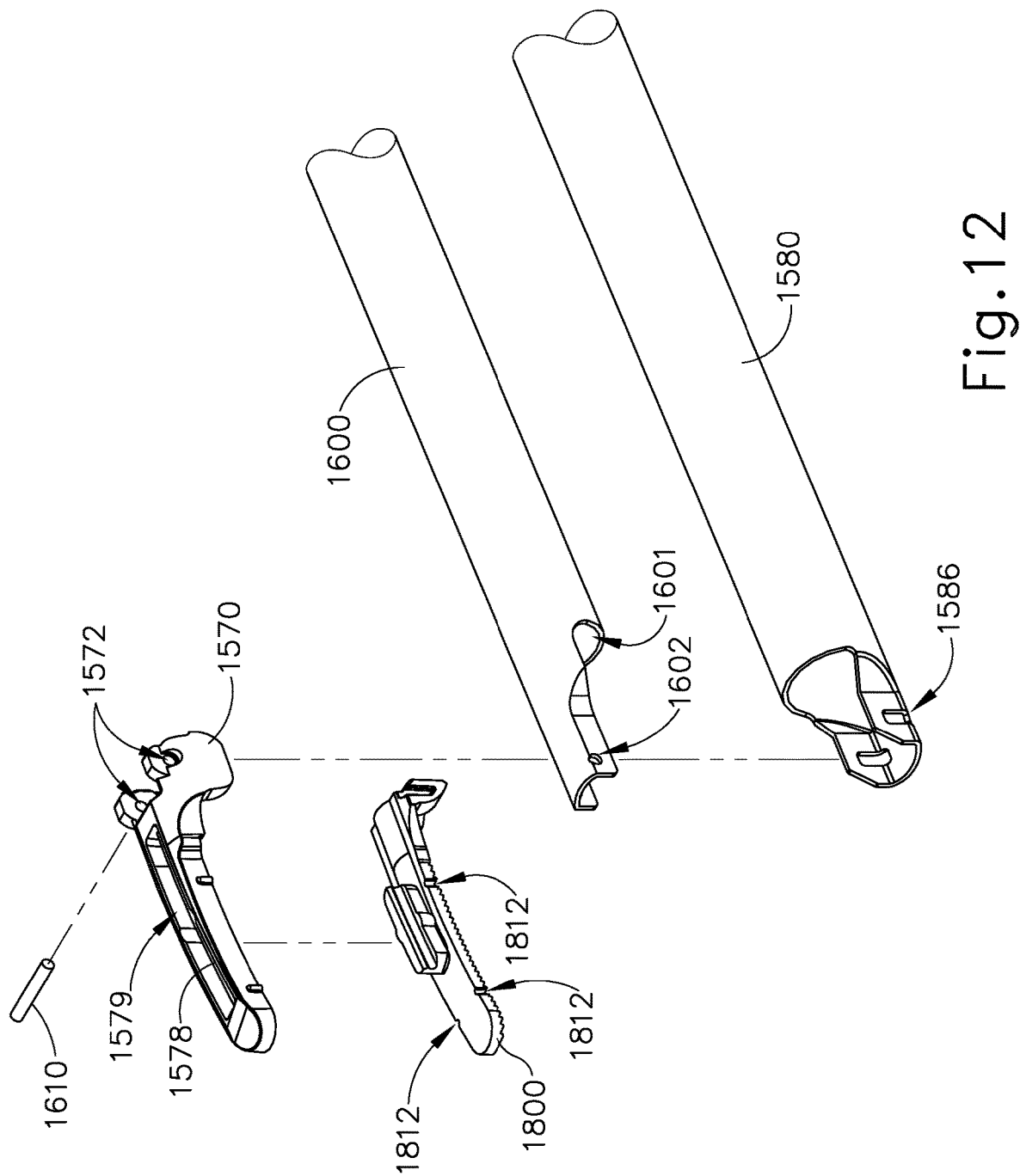
FIG. 12 depicts an exploded view of the distal end of the first disposable sub-assembly of FIG. 11.
Figure 13:
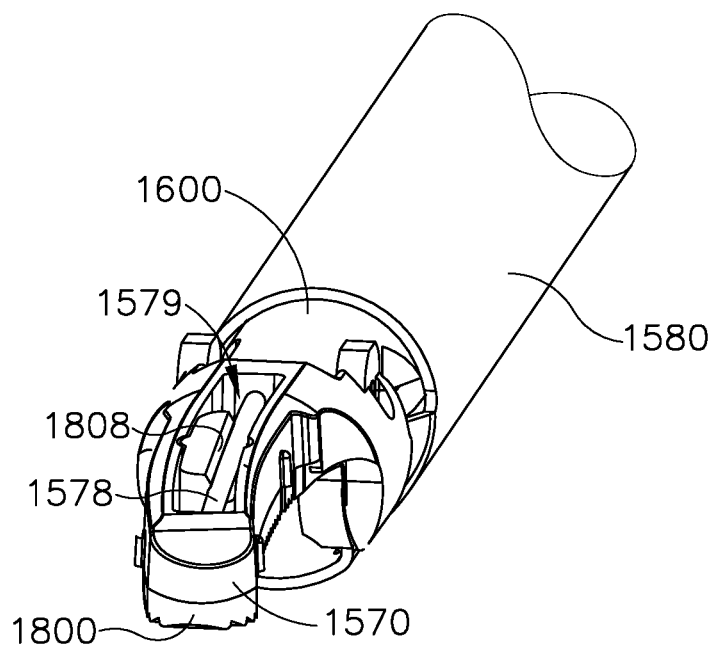
FIG. 13 depicts a perspective view of the distal end of the first disposable sub-assembly of FIG. 11.
Figure 14:
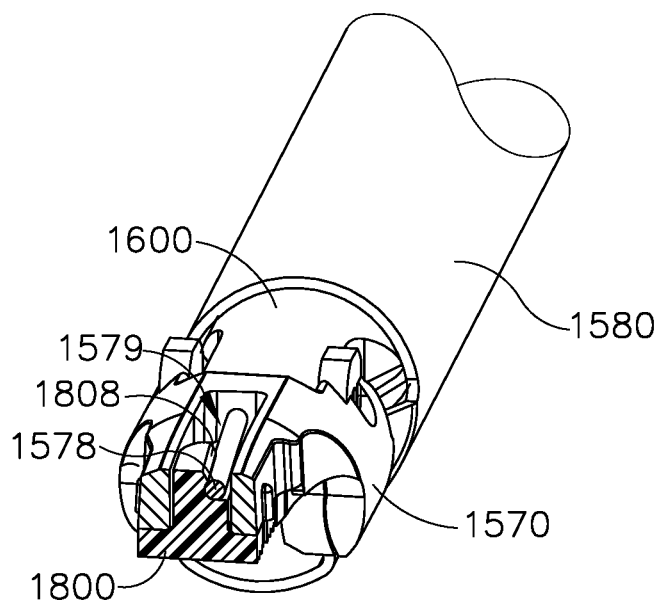
FIG. 14 depicts a cross sectional perspective view of the distal end of the first disposable sub-assembly of FIG. 13.
Figure 15A:
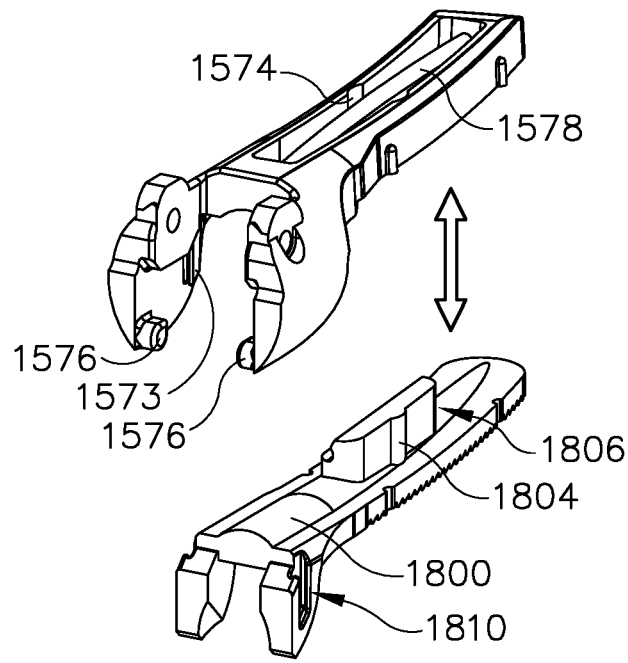
FIG. 15A depicts an exploded view of the clamp arm assembly of FIG. 8.
Figure 15B:
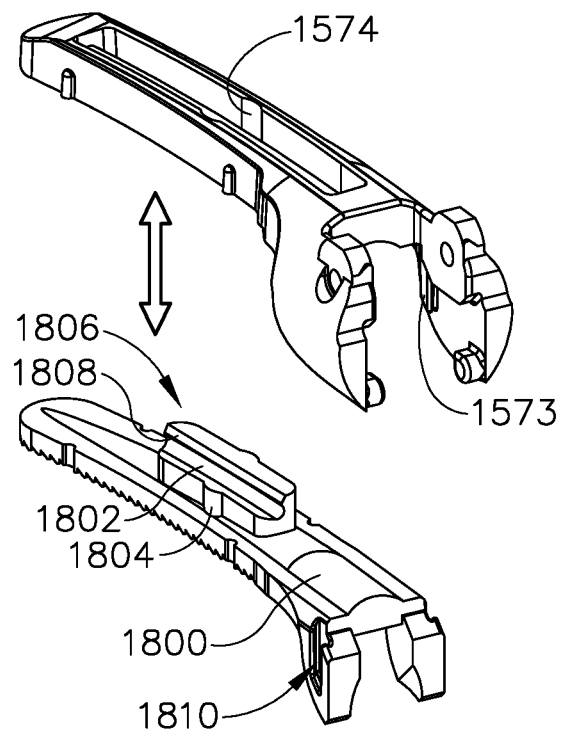
FIG. 15B depicts another exploded view of the clamp arm assembly of FIG. 8.

As shown in FIG. 12, inner tube member (1600) of the present example comprises an interior space (1601) configured to accommodate longitudinal travel of the distal end of ultrasonic blade (1560) during assembly of first disposable sub-assembly (1502) with second disposable sub-assembly (1504).

Figure 16:
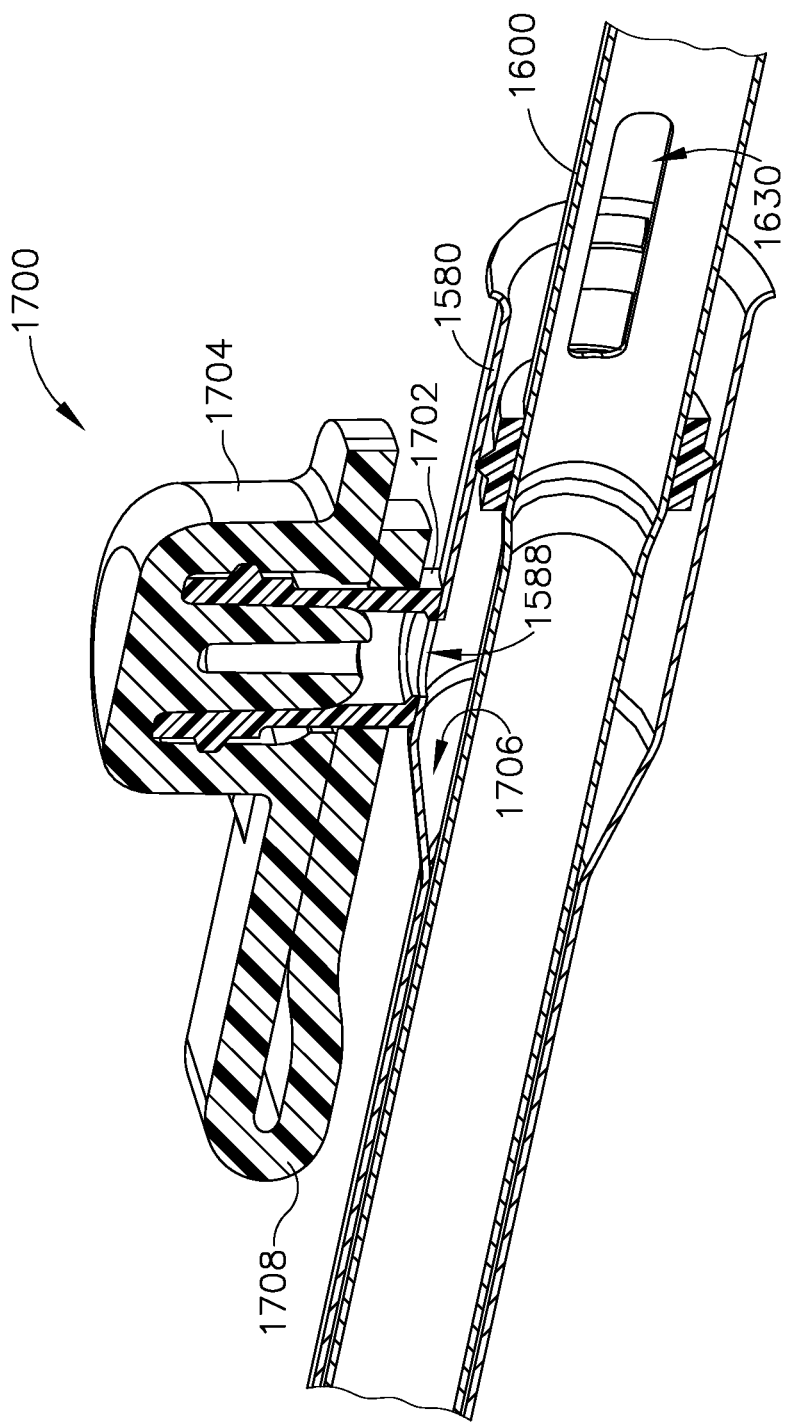
FIG. 16 depicts a cross sectional perspective view of a flush port assembly of the first disposable sub-assembly of FIG. 11.
Figure 17:
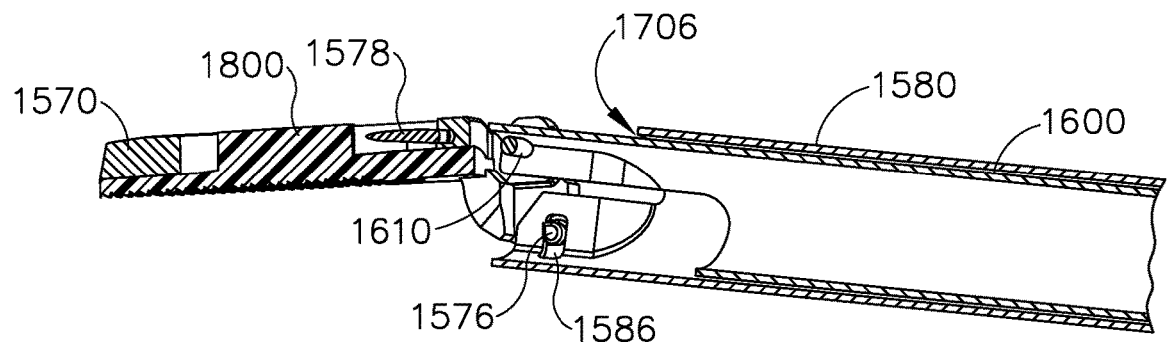
FIG. 17 depicts a cross sectional perspective view of the distal end of the first disposable sub-assembly of FIG. 11.

As shown in FIGS. 12, 16, and 17, outer tube (1580) is disposed about inner tube member (1600), such that outer tube (1580) is operable to translate longitudinally relative to inner tube member (1600) as mentioned above. Outer tube (1580) includes a flush port (1700) comprising a leer fitting (1702) and a cap (1704). Luer fitting (1702) connects with a lateral opening (1588) in outer tube (1580) that provides for fluid communication from outside outer tube (1580) to a passage (1706) formed between the inner diameter of outer tube (1580) and the outer diameter of inner tube (1600). Passage (1706) extends along the length of inner and outer tubes (1580, 1600). In operation, flush port (1700) allows for debris to be cleared from passage (1706) by way of rinsing, suction, and/or other ways that will be apparent to those of ordinary skill in the art in view of the teachings herein. In some instances, a fine cleaning instrument can be guided through passage (1706) by inserting the fine cleaning instrument within an open end of luer fitting (1702) once cap (1704) has been removed.

In the present example, cap (1704) includes a strap (1708) having an opening (1710) that is configured to fit around luer fitting (1702) as shown in FIG. 16. In this manner, cap (1704) remains connected with luer fitting (1702) when cap (1704) is removed from or installed upon luer fitting (1702). While strap (1708) is not depicted with opening (1710) around luer fitting (1702) in FIGS. 8 and 11, it is understood that strap (1708) is configurable such that strap (1708) is bendable in a U-shape such that opening (1710) is positionable around luer fitting (1702) as shown in FIG. 16, with cap (1704) then positionable on luer fitting (1702) to seal off access to passage (1706) through luer fitting (1702) during operation of the instrument in a surgical procedure (i.e., when first disposable sub-assembly (1502) is not being cleaned).

As shown in FIGS. 18A-18E, the proximal end of inner tube (1600) of the present example comprises a guide slot (1620). Guide slot (1620) is formed such that it extends laterally through the diameter of the proximal end of inner tube (1600) with a first slot opening (1621) on one side of inner tube (1600) and a second slot opening (1623) on the opposite side of inner tube (1600). In the present example, first guide opening (1621) is larger than second guide slot opening (1623) as will be discussed further below.

Guide slot (1620) includes a first portion (1622), a second portion (1624), and a third portion (1626). First portion (1622) extends longitudinally, while second portion (1624) extends helically, while third portion (1626) extends laterally. First and third portions (1622, 1626) are angularly offset from each other by approximately 90° about the longitudinal axis of inner tube (1600). Other suitable forms that guide slot (1620) may take will be apparent to those of ordinary skill in the art in view of the teachings herein.

As will be described in further detail below, outer tube (1580) is configured to couple with a tube actuator (1650) of second disposable sub-assembly (1504) when first disposable sub-assembly (1502) is coupled with second disposable sub-assembly (1504). Tube actuator (1650) is configured to drive outer tube (1580) longitudinally in response to pivotal movement of trigger (1512), to thereby drive clamp arm (1570) toward and away from blade (1560) as described above.

B. Exemplary Second Disposable Sub-Assembly

As shown in FIGS. 8-11, second disposable sub-assembly (1504) of the present example comprises a partial handle assembly (1510) having a pivoting trigger (1512), a set of buttons (1514, 1516), a coupling feature (1518), a communication feature (1519), and a knob member (1520). Knob member (1520) is rotatable relative to housing (1511) of partial handle assembly (1510). An acoustic waveguide (1562) extends distally from partial handle assembly (1510). Acoustic waveguide (1562) is coaxially disposed in inner tube (1600) and distally terminates in ultrasonic blade (1560). It should be understood that waveguide (1562) and blade (1560) may be configured and operable similar to waveguides (192, 562) and blades (190, 560) described above; and/or as described in any of the various references cited herein.

Figure 26A:
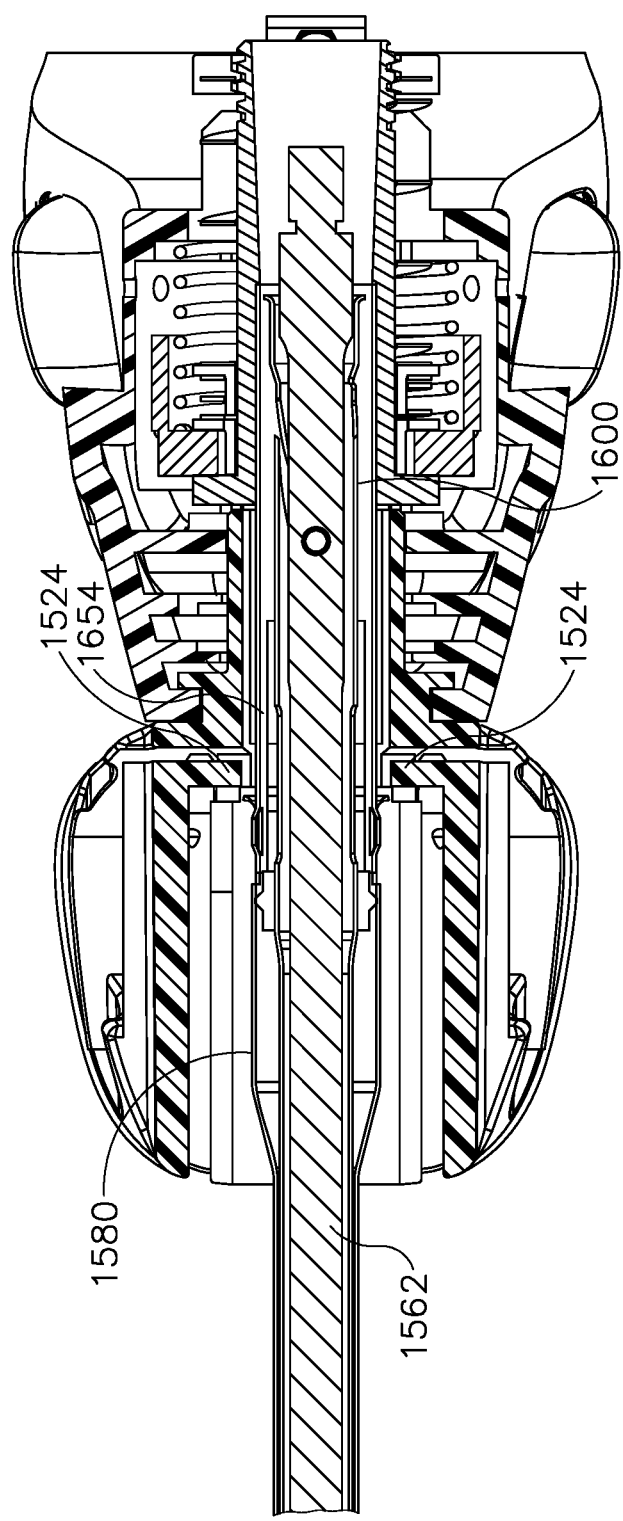
FIG. 26A depicts a cross sectional top view of the disposable portion of FIG. 8, before a process of disassembly with the clamp arm in a closed position.
Figure 26B:
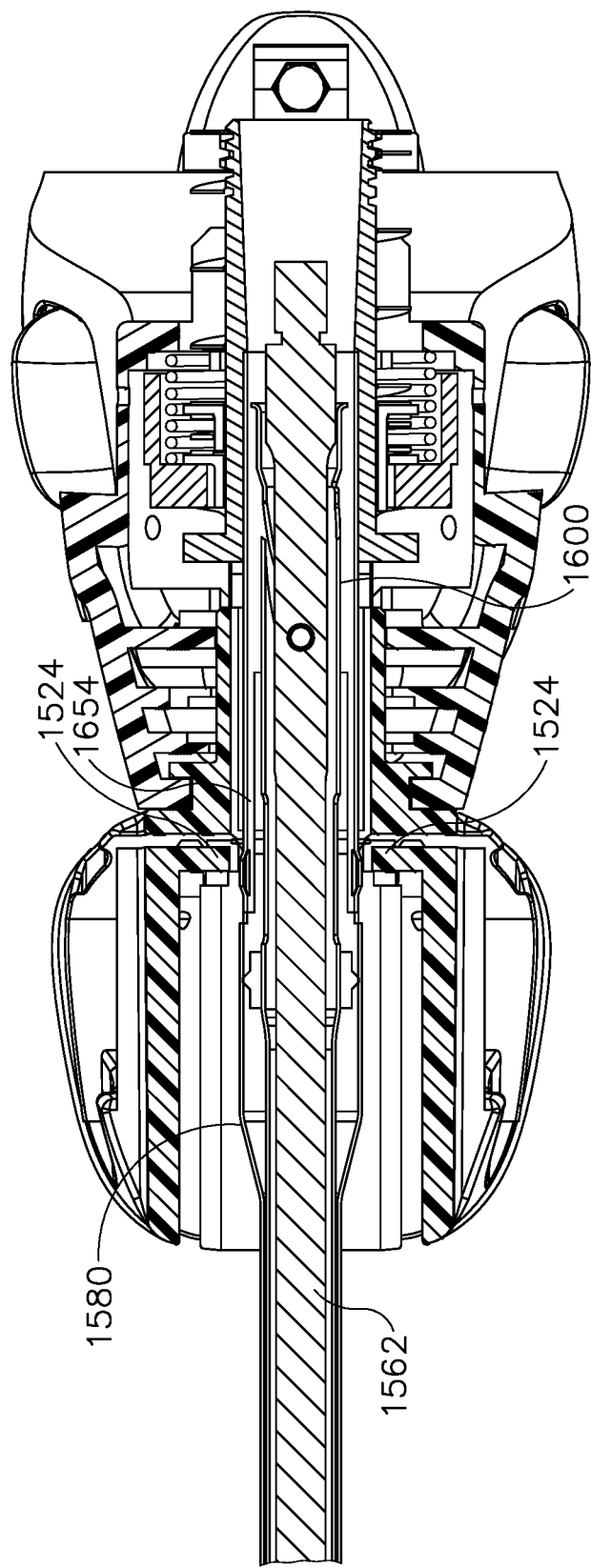
FIG. 26B depicts a cross sectional top view of the disposable portion of FIG. 8, before a process of disassembly with the clamp arm in an open position.
Figure 27:
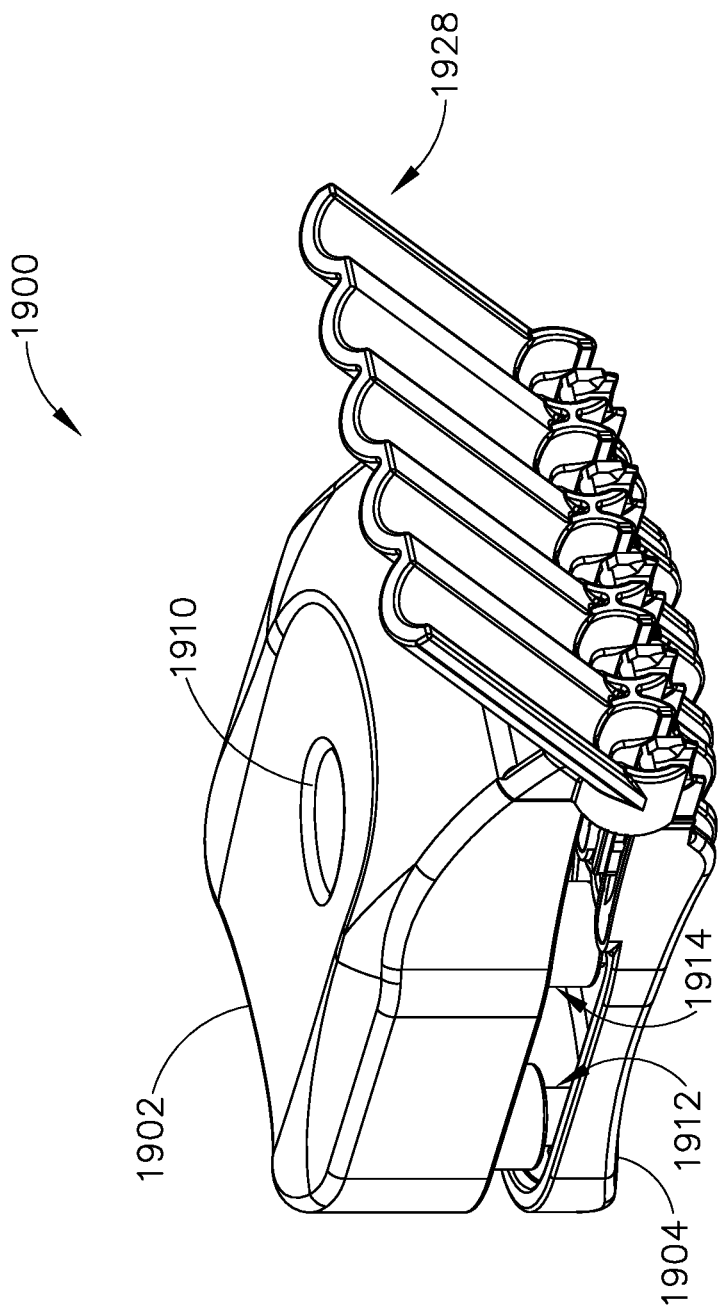
FIG. 27 depicts a perspective view of a clamp pad loader assembly.

In the present example, guide pin (1526) extends through waveguide (1562), thereby connecting waveguide (1562) with knob member (1520) as shown in FIGS. 26A-26B. As will be described in greater detail below, guide pin (1526) is also engaged with inner tube (1600) when assembly (1500) is fully assembled. Thus, as knob member (1520) is rotated relative to housing (1511), guide pin (1526) provides rotation of waveguide (1562) and inner tube (1600). Since the distal end of inner tube (1600) is coupled with the distal end of outer tube (1580) via clamp arm (1570), outer tube (1580) will rotate with inner tube (1600). Thus, rotation of knob member (1520) relative to housing (1511) will result in rotation of waveguide (1562) and the entire first disposable sub-assembly (1502) relative to housing (1511).

Trigger (1512) is operable to drive tube actuator (1650) longitudinally, to thereby drive outer tube (1580) longitudinally, to thereby drive clamp arm (1570) toward and away from blade (1560), when first disposable sub-assembly (1502) is coupled with second disposable sub-assembly (1504). Structural features of tube actuator (1650) will be described in greater detail below. Various suitable components that may be used to provide longitudinal movement of tube actuator (1650) in response to pivotal movement of trigger (1512) will be apparent to those of ordinary skill in the art in view of the teachings herein. By way of example only, trigger (1512) may be operatively coupled with tube actuator (1650) in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. In addition, or in the alternative, trigger (1512) may be operatively coupled with tube actuator (1650) in accordance with at least some of the teachings of U.S. Pub. No. 2016/0015419, entitled "Ultrasonic Surgical Instrument with Removable Handle Assembly," filed Sep. 29, 2015, issued as U.S. Pat. No. 10,349,967 on Jul. 16, 2019, the disclosure of which is incorporated by reference herein.

Buttons (1514, 1516) are operable to activate ultrasonic blade (1560). In particular, buttons (1514, 1516) are operable to activate the ultrasonic transducer assembly in the variation of reusable assembly (200), which in turn generates ultrasonic vibrations, which are communicated along waveguide (1562) to reach blade (1560). In some versions, button (1514) activates ultrasonic blade (1560) with ultrasonic energy at a first set of parameters (e.g., high power); while button (1516) activates ultrasonic blade (1560) with ultrasonic energy at a second set of parameters (e.g., low power). As another merely illustrative alternative, button (1514) may activate ultrasonic blade (1560) with ultrasonic energy; while button (1516) activates end effector (1550) to apply RF electrosurgical energy. Various suitable ways in which this may be carried out, as well as various other suitable ways in which buttons (1514, 1516) may be configured, arranged, and operable will be apparent to those of ordinary skill in the art in view of the teachings herein.

Coupling feature (1518) is operable to couple with one or more complementary coupling features in the variation of reusable assembly (200) in accordance with at least some of the teachings of U.S. Pub. No. 2015/0245850, issued as U.S.

Pat. No. 10,010,340, and/or in accordance with at least some of the teachings of U.S. Pub. No. 2016/0015419, issued as U.S. Pat. No. 10,349,967. In addition, or in the alternative, coupling feature (1518) may be actuated to transition disposable assembly (1500) into a cleaning mode in accordance with at least some of the teachings of U.S. Pub. No. 2015/0245850, issued as U.S. Pat. No. 10,010,340 and/or in accordance with at least some of the teachings of U.S. Pub. No. 2016/0015419, issued as U.S. Pat. No. 10,349,967. Various suitable components, features, and operabilities that may be incorporated into and/or otherwise associated with coupling feature (1518) will be apparent to those of ordinary skill in the art in view of the teachings herein.

Communication feature (1519) is operable to couple with one or more complementary coupling features in the variation of reusable assembly (200) in accordance with at least some of the teachings of U.S. Pub. No. 2015/0245850, issued as U.S. Pat. No. 10,010,340, and/or in accordance with at least some of the teachings of U.S. Pub. No. 2016/0015419 issued as U.S. Pat. No. 10,349,967. By way of example only, communication feature (1519) may comprise one or more electrical contacts that are operable to provide data communication and/or other electrical related operability when coupled with one or more complementary coupling features in the variation of reusable assembly (200). By way of example only, partial handle assembly (1510) may include sensors and/or various other kinds of features from which data may be provided to the variation of reusable assembly (200) via communication feature (1519). Various suitable components, features, and operabilities that may be incorporated into and/or otherwise associated with communication feature (1519) will be apparent to those of ordinary skill in the art in view of the teachings herein.

Figure 10A:
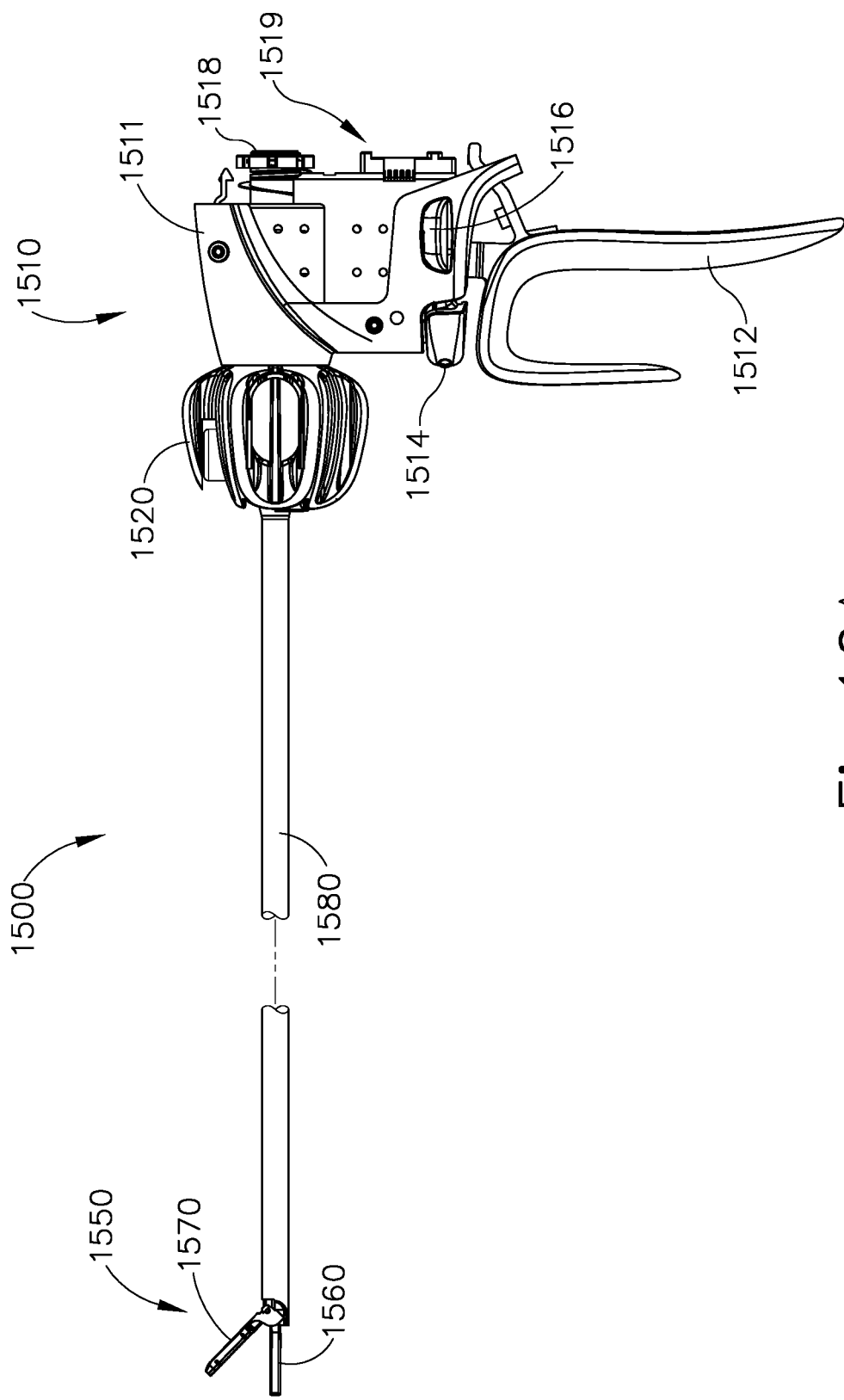
FIG. 10A depicts a side elevational view of the disposable portion of FIG. 8, with a portion of the shaft assembly omitted, and with the end effector in an open configuration.
Figure 10B:
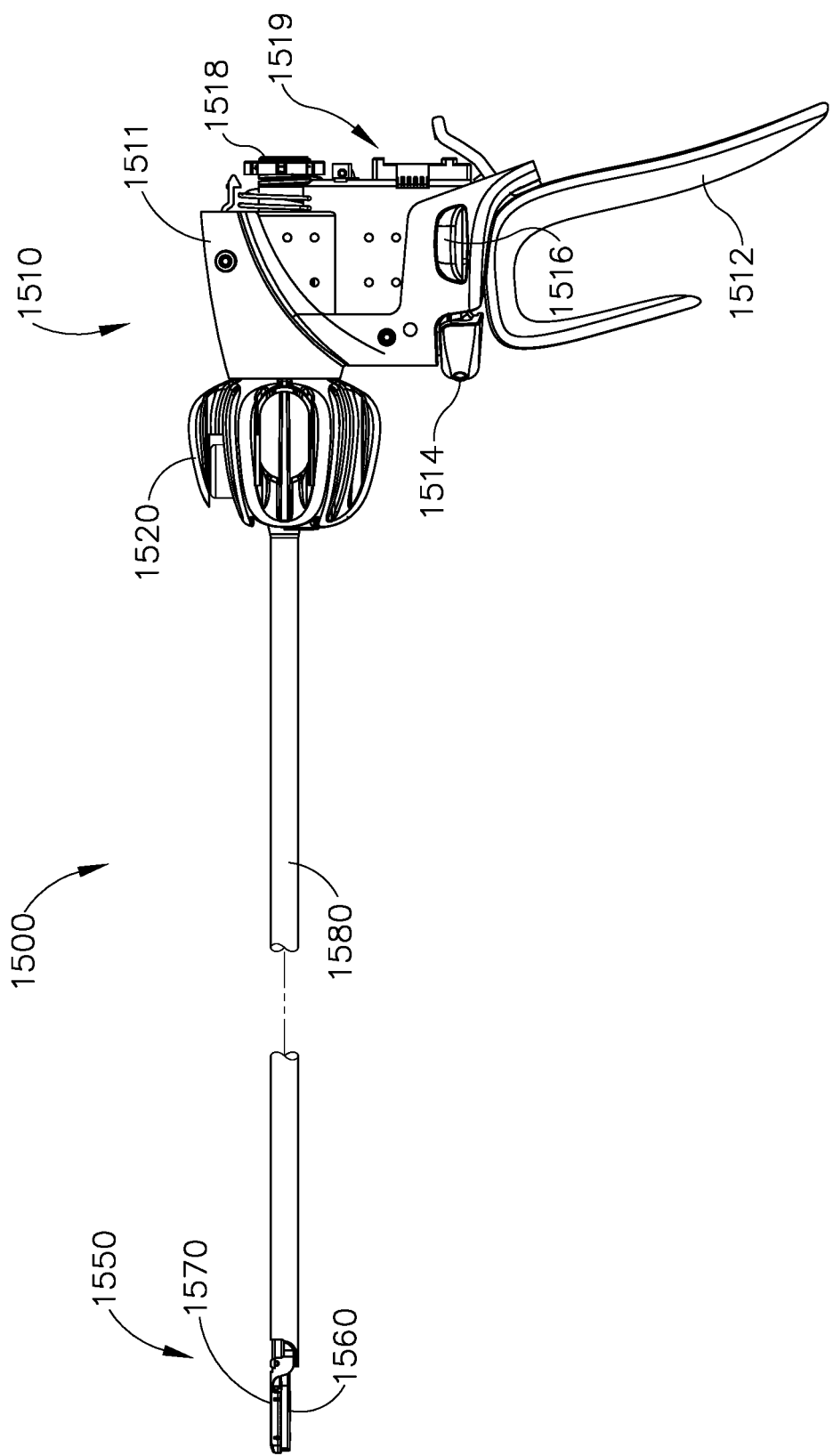
FIG. 10B depicts a side elevational view of the disposable portion of FIG. 8, with a portion of the shaft assembly omitted, and with the end effector in an closed configuration.
Figure 10C:
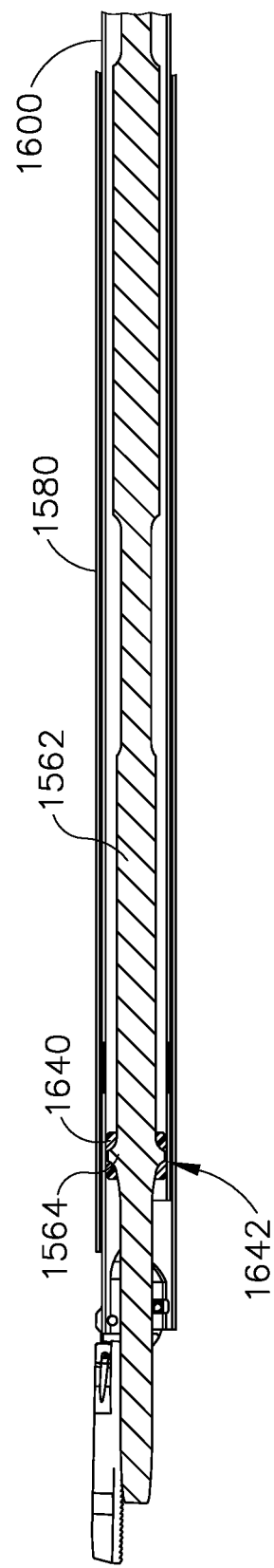
FIG. 10C depicts a cross sectional view of the distal portion of the disposable portion of FIG. 10B.
Figure 11:
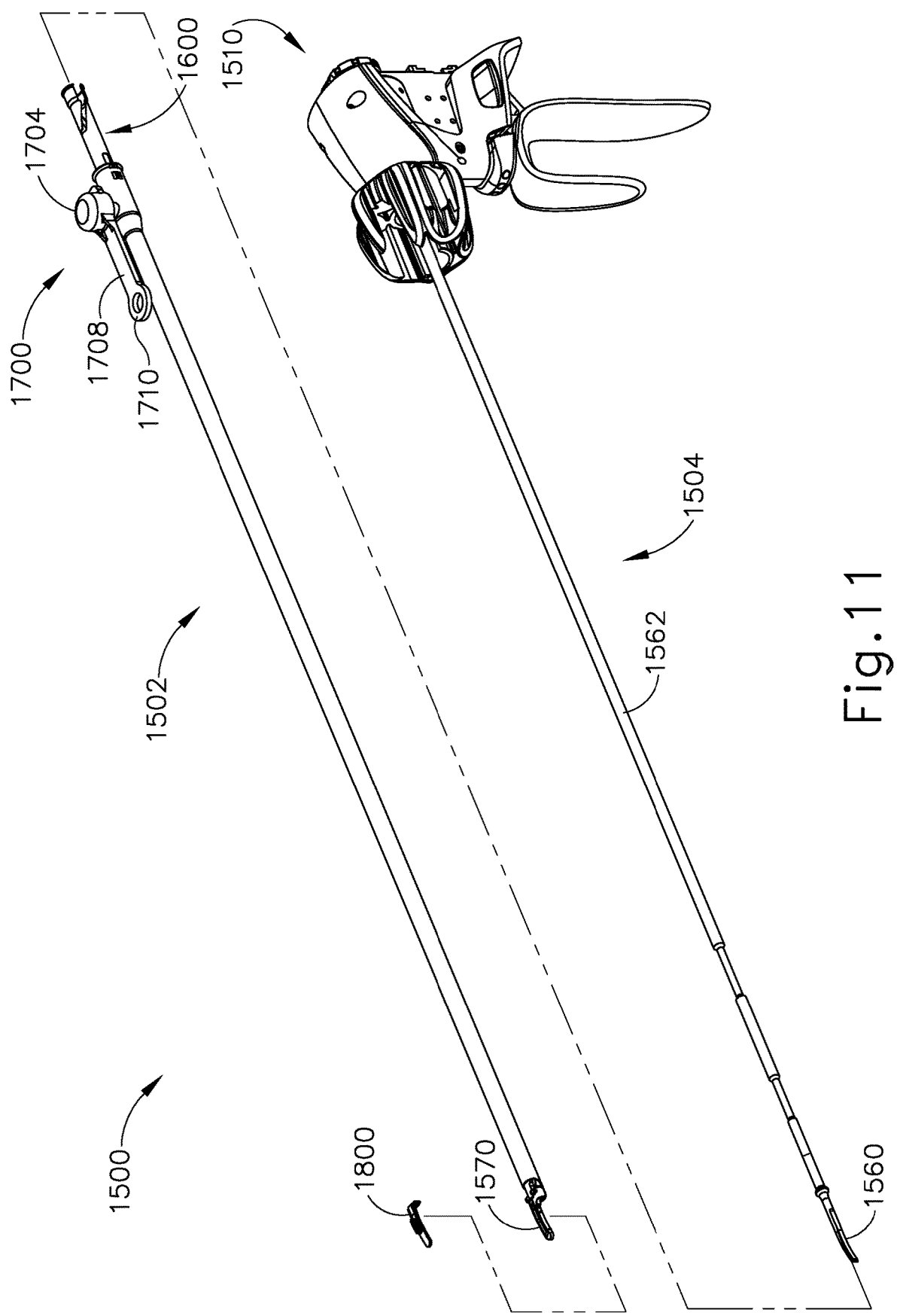
FIG. 11 depicts an exploded view of the disposable portion of FIG. 8, with a first disposable sub-assembly separated from a second disposable sub-assembly, and a disposable clamp pad further separated from the first disposable sub-assembly.

As best seen in FIGS. 10C and 11, inner tube (1600) is disposed coaxially about waveguide (1562) yet is radially spaced apart from waveguide (1562) such that inner tube (1600) does not contact waveguide (1562). As best seen in FIG. 10C, a seal member (1640) is coaxially interposed between the distal end of inner tube (1600) and waveguide (1562). Seal member (1640) comprises an inner annular groove (1642) that complements an annular collar (1564) formed in waveguide (1562). Seal member (1640) is formed of an elastomeric material and is located on waveguide (1562) at a longitudinal position corresponding to a node associated with resonant ultrasonic vibrations communicated through waveguide (1562). Seal member (1640) thus provides structural support between waveguide (1562) and inner tube (1600) without substantially interfering with ultrasonic vibrations through waveguide (1562). Seal member (1640) also prevents the ingress of fluids into the gap that is defined between inner tube (1600) and waveguide (1562). It should be understood that a series of elastomeric members may be interposed between inner tube (1600) and waveguide (1562), at longitudinal positions corresponding to a nodes associated with resonant ultrasonic vibrations communicated through waveguide (1562), though such elastomeric members may be configured differently from seal member (1640).

Figure 19:
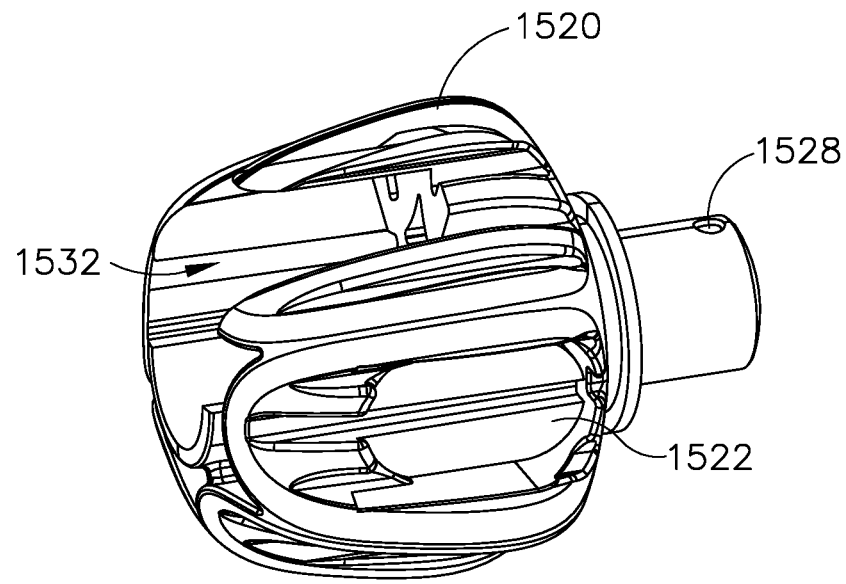
FIG. 19 depicts a perspective view of a knob member of the second disposable sub-assembly of FIG. 11.
Figure 20:
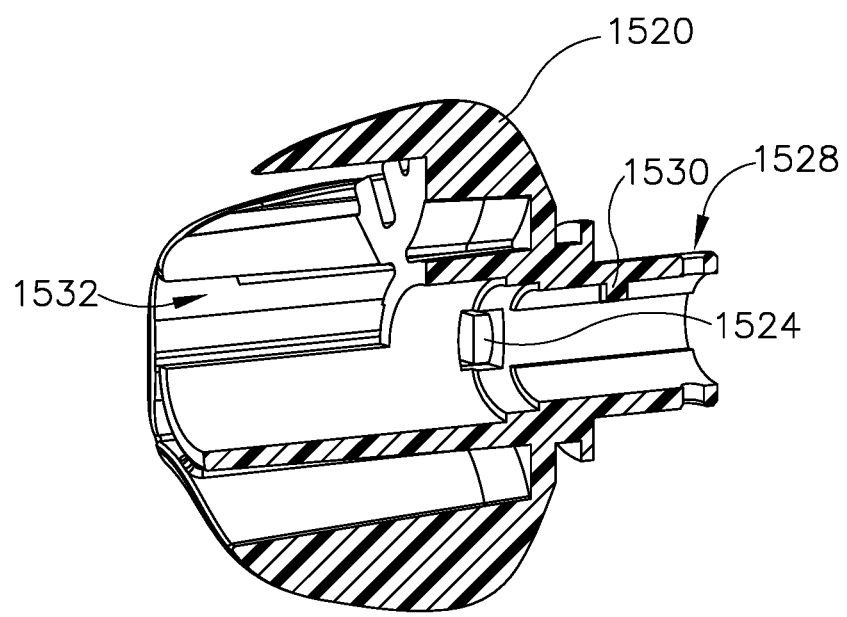
FIG. 20 depicts a cross sectional perspective view of the knob member of FIG. 19.
Figure 21:
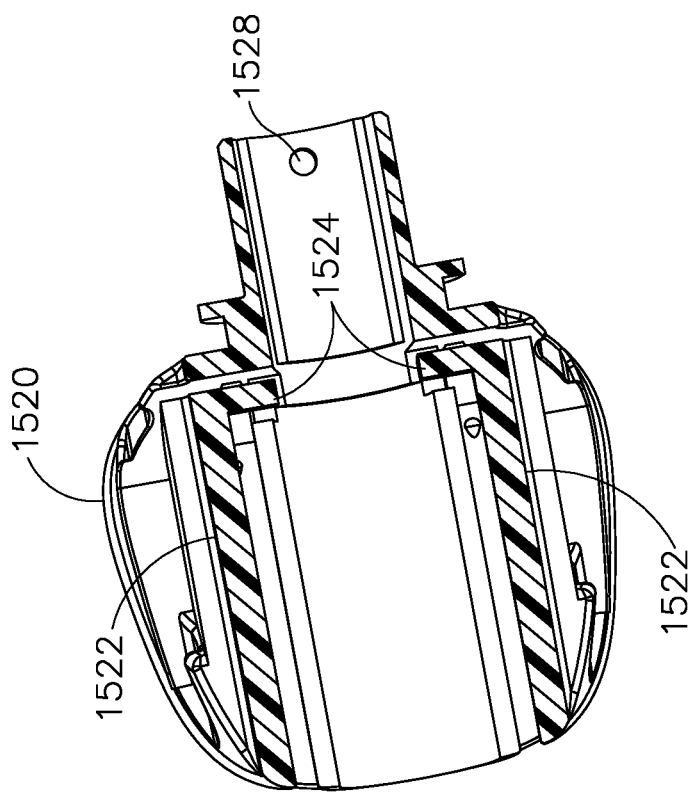
FIG. 21 depicts another cross sectional perspective view of the knob member of FIG. 19.

Knob member (1520) is operable to rotate the shaft assembly that is formed by waveguide (1562), inner tube (1600), outer tube (1580), and end effector (1550) when first disposable sub-assembly (1502) is coupled with second disposable sub-assembly (1504). In particular, this shaft assembly is rotatable relative to housing (1511) of partial handle assembly (1510). As best seen in FIGS. 19-21, knob member (1520) includes a pair of cantilevered buttons (1522). Each cantilevered button (1522) includes an inwardly projecting prong (1524). Buttons (1522) are operable to be pressed inwardly to thereby drive prongs (1524) inwardly, though buttons (1522) are resiliently biased to maintain the position of prongs (1524) as shown in FIG. 21. Guide pin (1526) (as seen in FIGS. 25A-25D) extends through a bore (1528) defined in knob member (1520). Guide pin (1526) is fixedly secured in knob member (1520) and is configured to interact with guide slot (1620) of inner tube (1600) during assembly and disassembly of sub-assemblies (1502, 1504) as will be described in greater detail below. As noted above, guide pin (1526) also couples waveguide (1562) with knob member (1520).

As shown in FIG. 20, knob member (1520) also comprises an inwardly extending boss (1530) that is configured to interact with guide slot (1620) of inner tube (1600) during assembly and disassembly of sub-assemblies (1502, 1504) as will be described in greater detail below. Knob member (1520) also includes recess (1532) that is configured to receive components of flush port (1700) as described above when first and second sub-assemblies (1502, 1504) are assembled. In this fashion, and as shown in FIG. 8-39B, flush port (1700) components are recessed within knob member (1520) when assembly (1500) is fully assembled.

Figure 22:
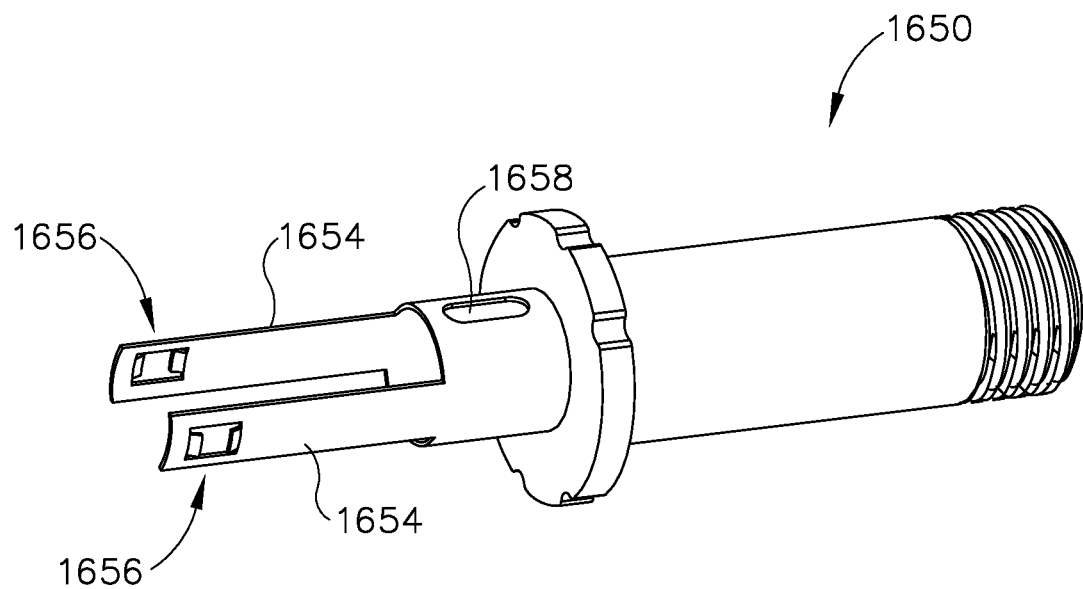
FIG. 22 depicts a perspective view of an outer tube actuator of the second disposable sub-assembly of FIG. 11.
Figure 23:
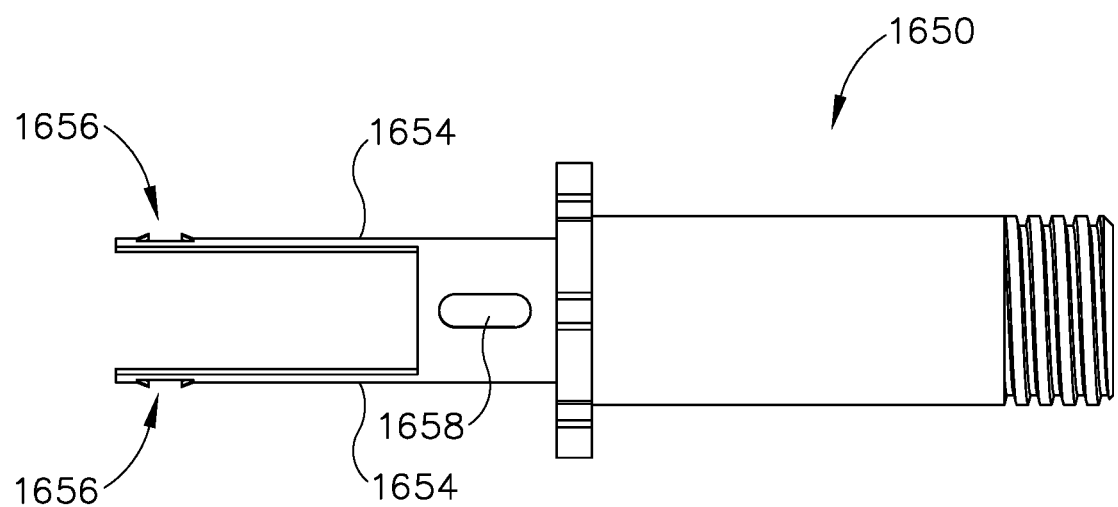
FIG. 23 depicts a top plan view of the outer tube actuator of FIG. 22.

As noted above, tube actuator (1650) is configured to removably couple with outer tube (1580) and thereby drive outer tube (1580) longitudinally in response to pivotal motion of trigger (1512). As best seen in FIGS. 22-23, tube actuator (1650) comprises a pair of distally projecting arms (1654). Each arm (1654) includes a pair of outwardly projecting prongs (1656). Each prong (1656) has chamfer, which promotes entry and exit of prongs (1656) into and out of corresponding pairs of openings (1582) of outer tube (1580) during assembly and disassembly of sub-assemblies (1502, 1504) as will be described in greater detail below. Arms (1654) are resiliently biased to assume a parallel relationship with each other as shown in FIG. 23. However, arms (1654) are configured to deform inwardly to enable entry and exit of prongs (1656) into and out of corresponding openings (1582) of outer tube (1580) during assembly and disassembly of sub-assemblies (1502, 1504) as will be described in greater detail below.

C. Exemplary Assembly of First Disposable Sub-Assembly with Second Disposable Sub-Assembly FIGS. 24A-25C show various stages of assembling first disposable sub-assembly (1502) with second disposable sub-assembly (1504). In particular, FIGS. 24A-25C show various stages occurring at the proximal end of first disposable sub-assembly (1502) during a process of assembling first disposable sub-assembly (1502) with second disposable sub-assembly (1504). It should be understood that during the process shown in FIGS. 24A-25C, an operator may grasp first disposable sub-assembly (1502) in one hand, grasp second disposable sub-assembly (1504) in the other hand, and then move first disposable sub-assembly (1502) relative to second disposable sub-assembly (1504) (while holding knob member (1520) stationary) in order to accomplish the process.

Figure 24A:
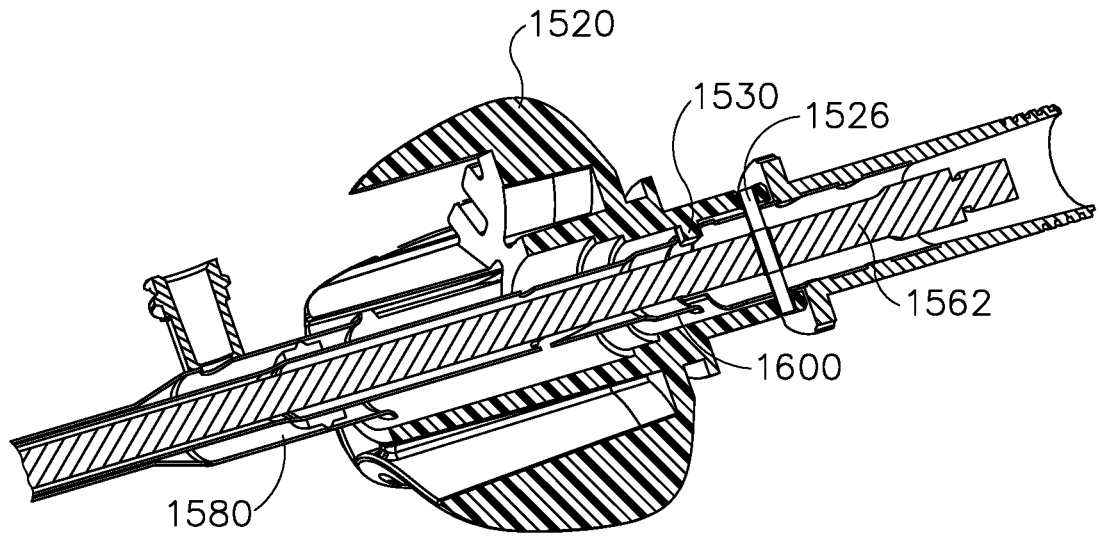
FIG. 24A depicts a partial cross sectional view of the disposable portion of FIG. 8, with the first disposable sub-assembly in a proximal position before a guide slot of the inner tube has engaged a guide pin of the knob member, and before the guide slot of the inner tube has engaged a projecting member of the knob member during the process of assembly.

Beginning with FIG. 24A, first disposable sub-assembly (1502) is aligned coaxially with waveguide (1562) of second disposable sub-assembly (1504) and then moved proximally relative to second disposable sub-assembly (1504) such that waveguide (1562) is inserted within inner tube (1600). This proximal movement of first disposable sub-assembly (1502) relative to second disposable sub-assembly (1504) continues until the point shown in FIG. 24A, where the proximal end of inner tube (1600) abuts boss (1530) within knob member (1520).

Figure 24B:
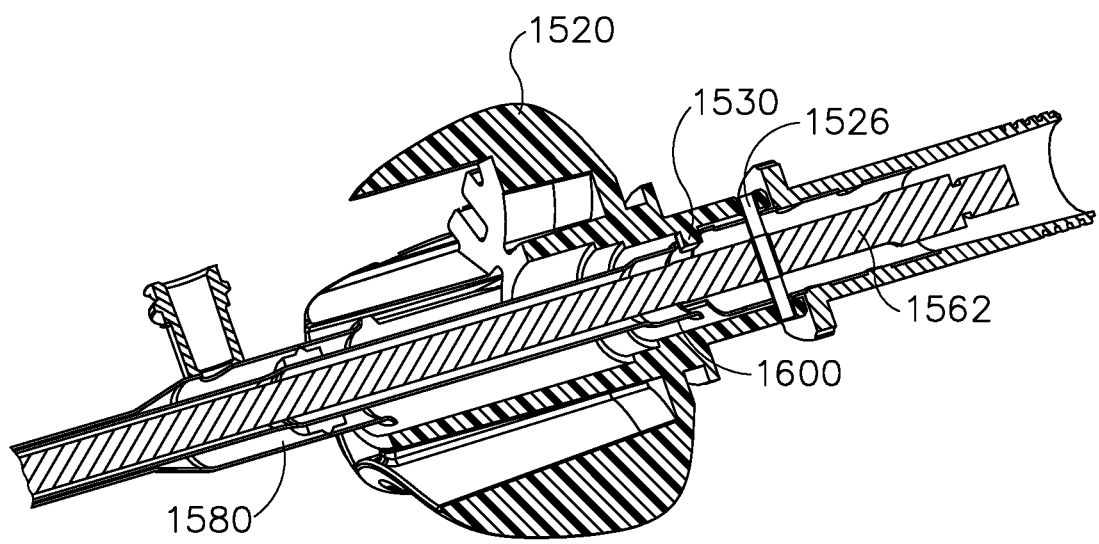
FIG. 24B depicts a partial cross sectional view of the disposable portion of FIG. 8, with the first disposable sub-assembly in the proximal position before the guide slot of the inner tube has engaged the guide pin of the knob member, and before the guide slot of the inner tube has engaged the projecting member of the knob member, but with the inner tube rotated to register the projecting member of the knob member with an enlarged slot portion of the guide slot of the inner tube during the process of assembly.

To ensure proper alignment of curved clamp arm (1570) with curved blade (1560), boss (1530) is sized to match first slot opening (1621) of guide slot (1620). With this configuration, boss (1530) is too large compared to second slot opening (1623) to fit within second slot opening (1623). Therefore, installing first disposable sub-assembly (1502) onto second disposable sub-assembly (1504) will only occur when boss (1530) is angularly aligned with the correct slot opening—first slot opening (1621) in the present example. Referring to FIG. 24B, inner tube (1600) has been rotated to align first slot opening (1621) with boss (1530).

Figure 18A:
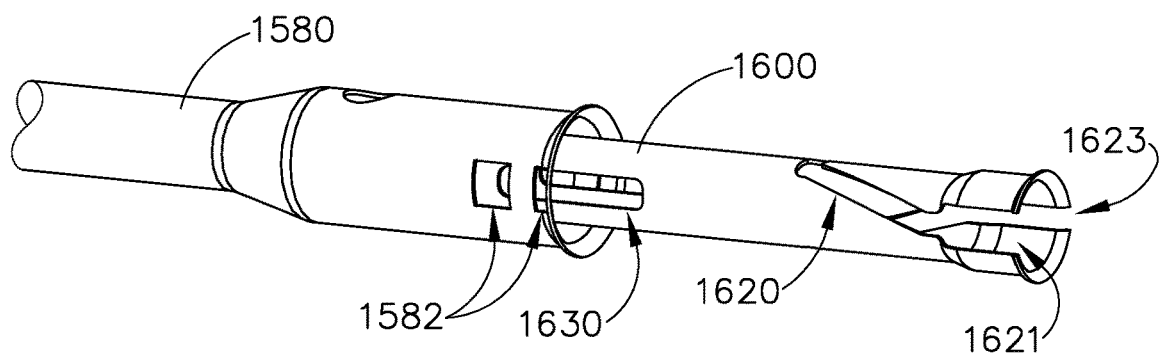
FIG. 18A depicts a perspective view of the proximal ends of the inner tube and outer tube of the first disposable sub-assembly of FIG. 11.
Figure 18B:
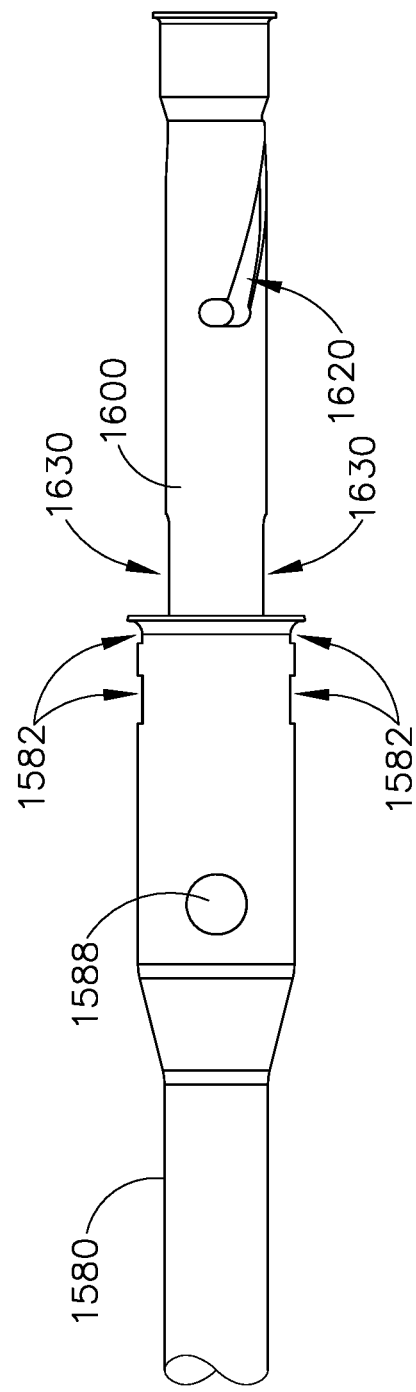
FIG. 18B depicts a top view of the proximal ends of the inner tube and outer tube of the first disposable sub-assembly of FIG. 11.
Figure 18C:
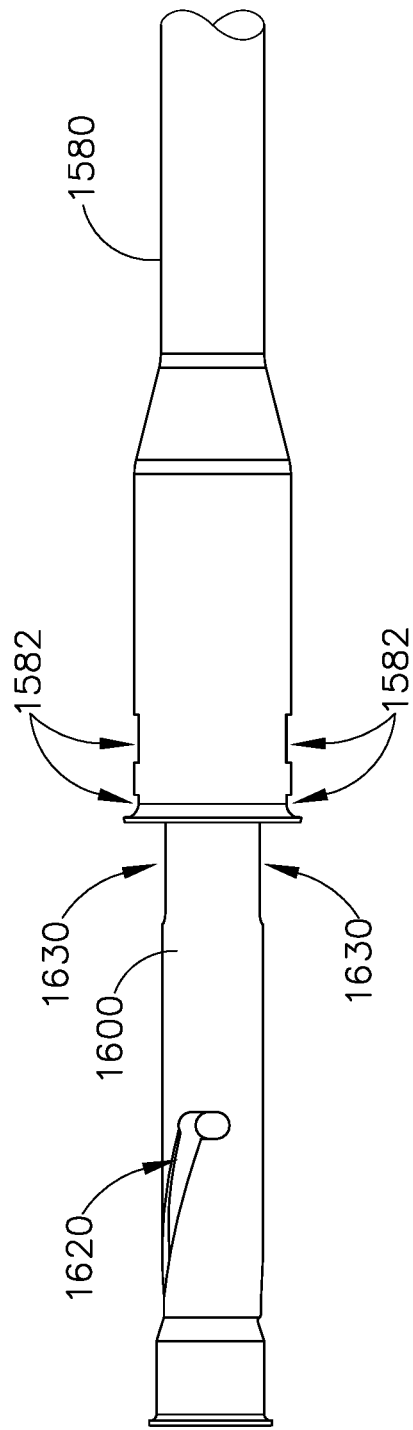
FIG. 18C depicts a bottom view of the proximal ends of the inner tube and outer tube of the first disposable sub-assembly of FIG. 11.
Figure 24C:
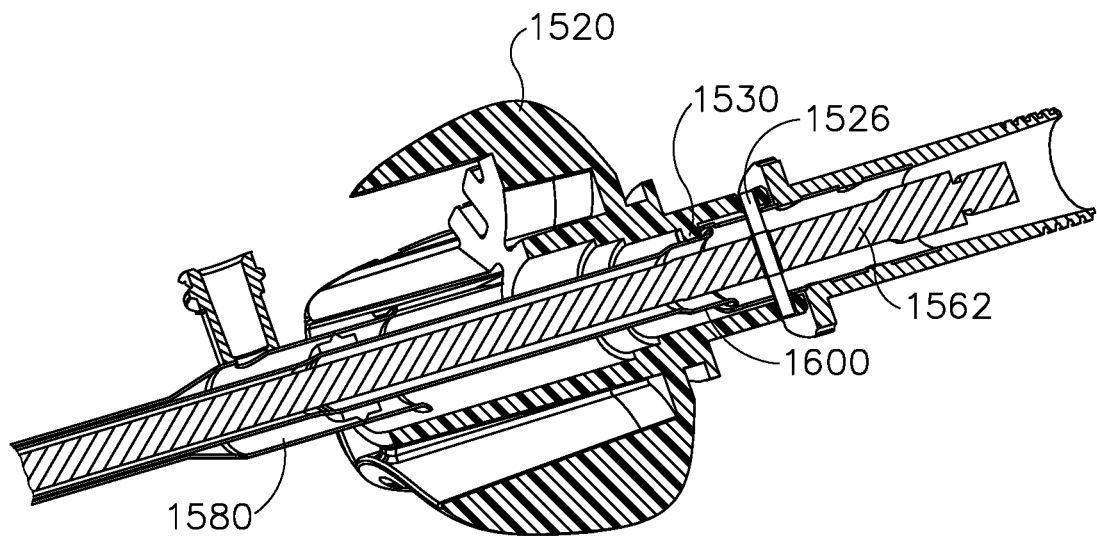
FIG. 24C depicts a partial cross sectional view of the disposable portion of FIG. 8, with the first disposable sub-assembly in a proximal position before the guide slot of the inner tube has engaged the guide pin of the knob member, and after the guide slot of the inner tube has engaged the projecting member of the knob member during the process of assembly.

As shown in FIG. 24C, first disposable sub-assembly (1502) is advanced further proximally relative to second disposable sub-assembly (1504) as boss (1530) is received within first portion (1622) of guide slot (1620). Referring also to FIGS. 18A and 18D, first slot opening (1621) of guide slot (1620) reduces in width as first portion (1622) of guide slot (1620) transitions to second portion (1624) of guide slot (1620). At about the same location, the proximal end of inner tube (1600) reduces in diameter from a first diameter along the region of inner tube (1600) that extends with first portion (1622) of guide slot (1620) to a second diameter along the remainder of inner tube (1600) that extends with second and third portions (1624, 1626) of guide slot (1620). This change in diameter allows boss (1530) to initially be insertable within first portion (1622) of guide slot (1620), and then to move outside of guide slot (1620) once the second portion (1624) of guide slot (1620) reaches boss (1530). FIG. 25D shows when first disposable sub-assembly (1502) is fully coupled with second disposable sub-assembly (1504) and boss (1530) is located along the outside surface of inner tube (1600).

Figure 24D:
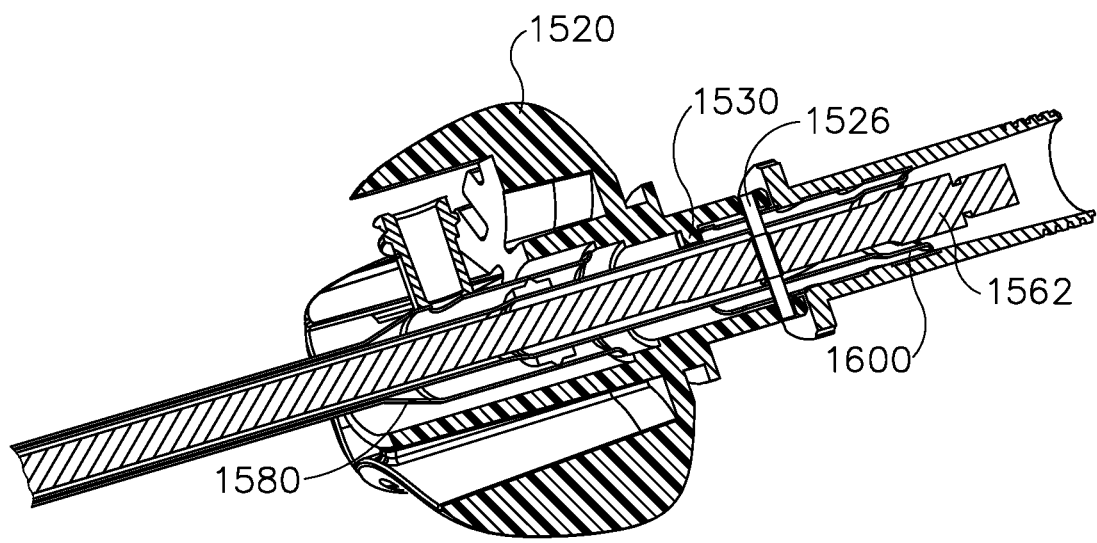
FIG. 24D depicts a partial cross sectional view of the disposable portion of FIG. 8, with the first disposable sub-assembly in a fully coupled proximal position upon completion of the process of assembly.

In between the assembly stages shown in FIGS. 24C and 24D, guide slot (1620) engages with guide pin (1526). In some versions, the distance between boss (1530) and guide pin (1526) is the same or substantially the same as the longitudinal distance along the larger diameter region of inner tube (1600) that extends along first portion (1622) of guide slot (1620). In this arrangement, as boss (1530) transitions from within guide slot (1526) to outside of guide slot (1526), guide slot (1526) engages guide pin (1526). It should be understood that in other versions, it is not required that these distances are the same or substantially the same such that guide slot (1620) is not required to engage with guide pin (1526) at the same time as boss (1530) disengages from guide slot (620).

Figure 25A:
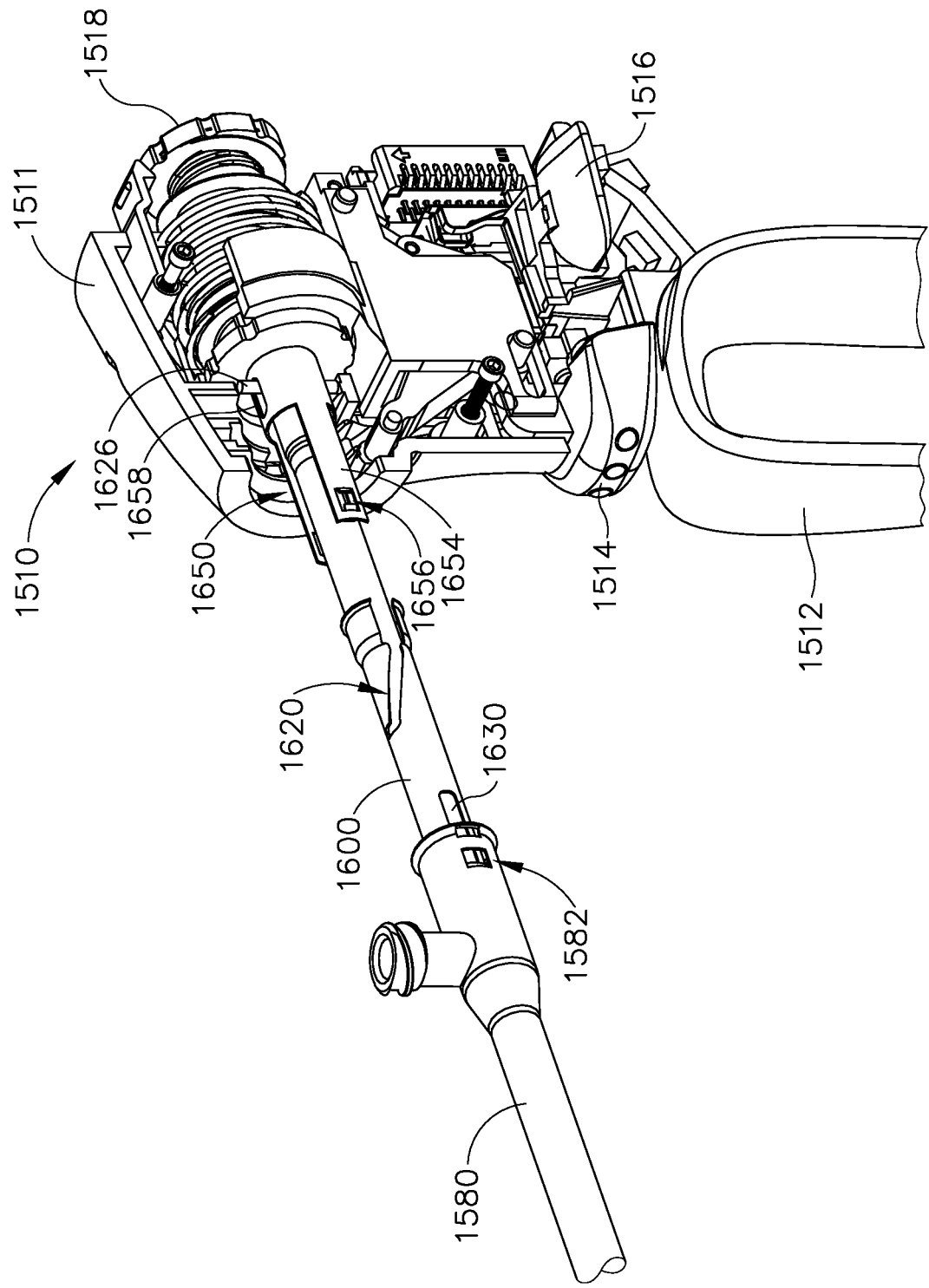
FIG. 25A depicts a partial view of the disposable portion of FIG. 8, with the knob member omitted to reveal internal components, with the first disposable sub-assembly in a distal position before a guide slot of the inner tube has engaged a guide pin of the knob member during e process of assembly.
Figure 25B:
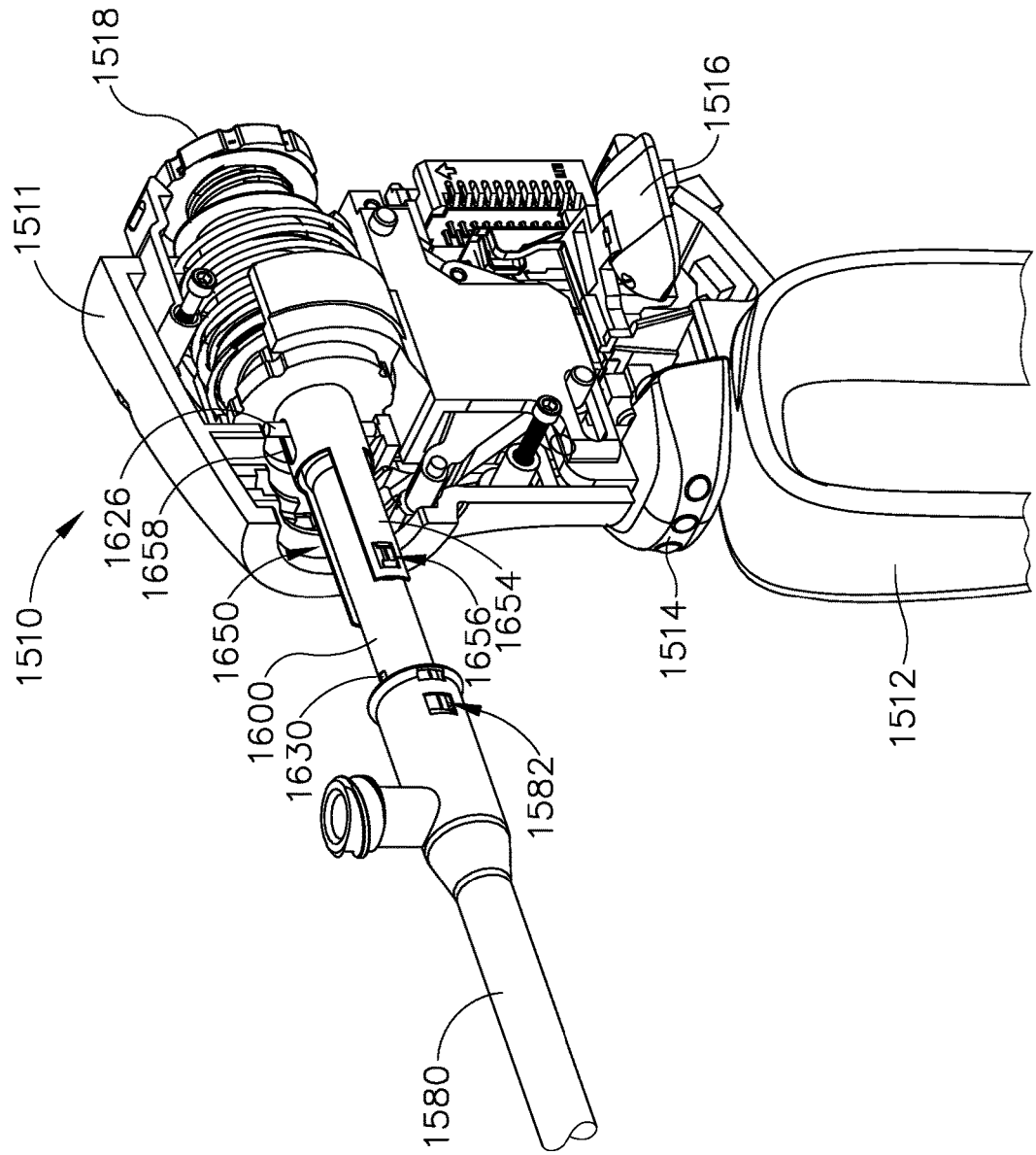
FIG. 25B depicts a partial view of the disposable portion of FIG. 8, with the knob member omitted to reveal internal components, with the first disposable sub-assembly in a proximal position whereby the guide pin has traversed a first portion of the guide slot in the inner tube during the process of assembly.
Figure 25C:
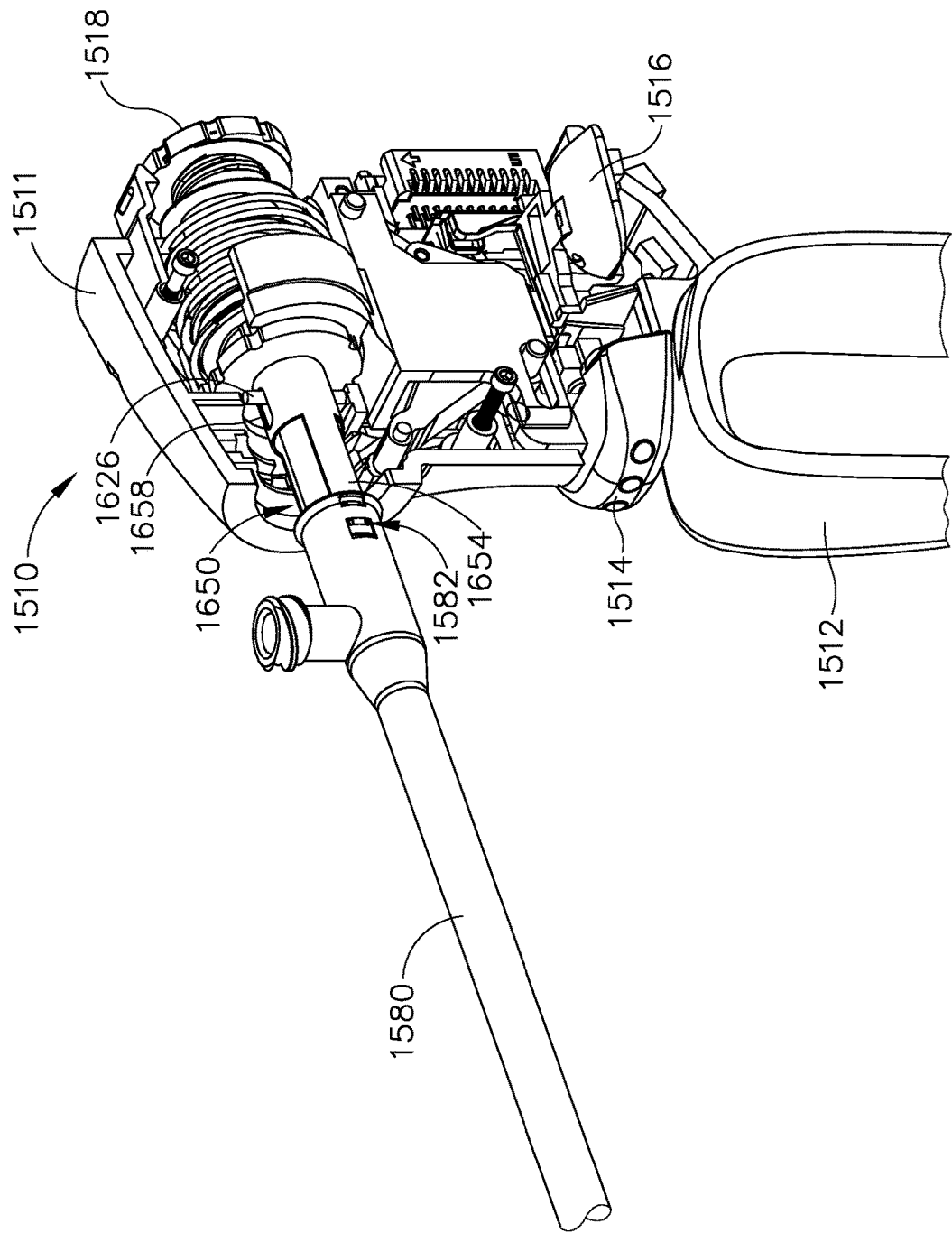
FIG. 25C depicts a partial view of the disposable portion of FIG. 8, with the knob member omitted to reveal internal components, with the first disposable sub-assembly in a fully coupled proximal position upon completion of the process of assembly.

FIGS. 25A-25C show another series of views similar to the series shown in FIGS. 24A-24D, but with knob member (1520) omitted in order to enable visualization of the components that would otherwise be obscured by knob member (1520). For reference, FIG. 25C shows the same final stage of assembly as is shown in FIG. 24D. As shown in FIG. 25A, first disposable sub-assembly (1502) is at a distal position. At this stage, the proximal end of inner tube (1600) is distal to guide pin (1526). It should be noted that FIG. 25A also shows how the proximal end of outer tube member (1580) includes pairs of openings (1582) that accommodates features of second disposable sub-assembly (1504), such as outwardly projecting prongs (1656) of the distal ends of arms (1654).

FIG. 25B shows a stage where first disposable sub-assembly (1502) has been translated proximally to a point where guide pin (1526) has traversed first portion (1622) of guide slot (1620) in inner tube (1600). As described above, it should be understood that boss (1530) of knob member (1520) provides the angular alignment of first disposable sub-assembly (1502) relative to second disposable sub-assembly (1504) that would be required in order for guide pin (1526) to successfully enter first portion (1622) of guide slot (1620) during the transition to the state shown in FIG. 25B. At the stage shown in FIG. 25B, openings (1582) of outer tube (1580) area still distal to prongs (1656) of tube actuator (1650).

FIG. 25C shows a stage where first disposable sub-assembly (1502) has been translated proximally and inner tube (1600) of first disposable sub-assembly (1502) rotated about the longitudinal axis to a point where guide pin (1526) has traversed second and third portions (1624, 1626) of guide slot (1620) in inner tube (1600). During the transition from the state shown in FIG. 25B to the state shown in FIG. 25C, inner tube (1600) of first disposable sub-assembly (1502) has rotated 90° relative to second disposable sub-assembly (1504), about the longitudinal axis of waveguide (1562). Outer tube (1580) rotates 90° with inner tube (1600) during the transition from the state shown in FIG. 25B to the state shown in FIG. 25C, due to the fact that the distal ends of tubes (1580, 1600) are coupled together by clamp arm (1570). Upon completing the 90° rotation, openings (1582) of outer tube (1580) are angularly aligned with arms (1654) of tube actuator (1650), and flush port (1700) of outer tube (1582) aligns with recess (1532) of knob member (1520).

During the transition from the state shown in FIG. 25B to the state shown in FIG. 25C, the proximal end of outer tube (1580) has deflected the distal ends of arms (1654) inwardly, thereby driving prongs (1656) inwardly. This deflection is accommodated by longitudinally extending slots (1630) of proximal inner tube (1600). When outer tube (1580) reaches the longitudinal position where prongs (1656) are aligned with openings (1582), the resilience of arms (1654) drives prongs (1656) outwardly such that prongs (1656) snap into place in openings (1582).

With assembly completed as shown in FIG. 25C, at this stage outer tube (1580) coupled with tube actuator (1650) such that outer tube (1580) will translate longitudinally with tube actuator (1650). A slot (1658) is dimensioned to enable tube actuator (1650), and thus connected outer tube (1580), to translate relative to guide pin (1526) during the translation of outer tube (1580) that would be required to pivot clamp arm (1570) toward and away from blade (1560) as described above. At this stage, sub-assemblies (1502, 1504) are coupled together such that disposable assembly (1500) is ready for assembly with the variation of reusable assembly (200).

In the series shown in FIGS. 24A-25C, second disposable sub-assembly (1504) appears to remain fixed in place while first disposable sub-assembly (1502) moves. However, it should be understood that an operator may in fact hold first disposable sub-assembly (1502) stationary and move second disposable sub-assembly (1504) In order to transition through the stages shown in FIGS. 24A-25C.

D. Exemplary Disassembly of First Disposable Sub-Assembly from Second Disposable Sub-Assembly As noted above, first disposable sub-assembly (1502) may be configured for 5 uses while second disposable sub-assembly (1504) may be configured for 5 to 10 uses (or any other suitable number of uses). It may therefore be desirable to enable an operator to disassemble first disposable sub-assembly (1502) from second disposable sub-assembly (1504) without destroying second disposable sub-assembly (1504). To that end, FIGS. 26A-26B show various stages of disassembling first disposable sub-assembly (1502) from second disposable sub-assembly (1504). In particular, FIGS. 26A-26B show various stages occurring at the proximal end of assembled first and second disposable sub-assemblies (1502, 1504) during a process of disassembling first disposable sub-assembly (1502) from second disposable sub-assembly (1504).

As shown in FIG. 26A, when clamp arm (1570) is in a closed or clamped position from retraction of outer tube (1580) proximally based upon actuation of trigger (1512), prongs (1524) of knob member (1520) are located at positions adjacent the proximal end of outer tube (1580). In this position, actuating cantilevered buttons (1522) of knob member (1520) to drive prongs (1524) toward arms (1654) of tube actuator (1650) will cause prongs (1524) to contact the proximal end of outer tube (1580) instead of arms (1654). This longitudinal offset may prevent an operator from inadvertently disengaging prongs (1656) from outer tube (1580) during use of disposable assembly (1500) in a fully assembled instrument.

In order to initiate disassembly, the operator may need to first actuate trigger (1512) in a fashion that extends outer tube (1580) distally to open clamp arm (1570). FIG. 26B shows the position of outer tube (1580) and tube actuator (1650) when clamp arm (1570) is open compared to the position of prongs (1524) of knob member (1520). Once outer tube (1580) and tube actuator (1650) have been translated distally to the position shown in FIG. 26B, prongs (1524) of knob member (1520) are aligned with arms (1654) of tube actuator (1650), though prongs (1524) of knob member (1520) are laterally spaced form arms (1654) of tube actuator (1650). In some variations, prongs (1524) of knob member (1520) are aligned with arms (1654) of tube actuator (650) during normal use of disposable assembly (1500) in a fully assembled instrument, regardless of whether clamp arm (1570) is in an open or closed position.

Once in the position shown in FIG. 26B, the operator may press cantilevered buttons (1522) inwardly. In this example, both buttons (1522) are pressed inwardly simultaneously. This drives prongs (1524) inwardly. As prongs (1524) move inwardly, prongs (1524) bear against arms (1654), thereby deflecting the distal ends of arms (1654) inwardly. This deflection at least partially unseats prongs (1656) from openings (1582) in outer tube (1580). With prongs (1656) at least partially unseated from openings (1582) in outer tube (1580), the operator may pull distally on first disposable sub-assembly (1502) while holding second disposable sub-assembly (1504) stationary (while still pressing cantilevered buttons (1522) inwardly). This will ultimately result in the proximal end of outer tube (1580) clearing prongs (1656) of tube actuator (1650) such that outer tube (1580) is separated or disassembled from tube actuator (1650). With outer tube (1580) clear of prongs (1656), arms (1654) may resiliently transition back to the straight, parallel orientations as shown in FIG. 23. In addition, with outer tube (1580) clear of prongs (1656), the operator is free to pull first disposable sub-assembly (1502) clear from the remainder of second disposable sub-assembly (1504). The operator may then clean, sterilize, or dispose of first disposable sub-assembly (1502), and clean, sterilize, and re-use second disposable sub-assembly (1504) if appropriate.

It should be understood that during the process of disassembly shown in FIGS. 26A-26B, inner tube (1600) of first disposable sub-assembly (1502) may rotate relative to second disposable sub-assembly (1504), about the longitudinal axis of waveguide (562), due to interaction between guide pin (1526) and guide slot (1620) as described above.

E. Clamp Pad Removal and Reloading

Figure 29:
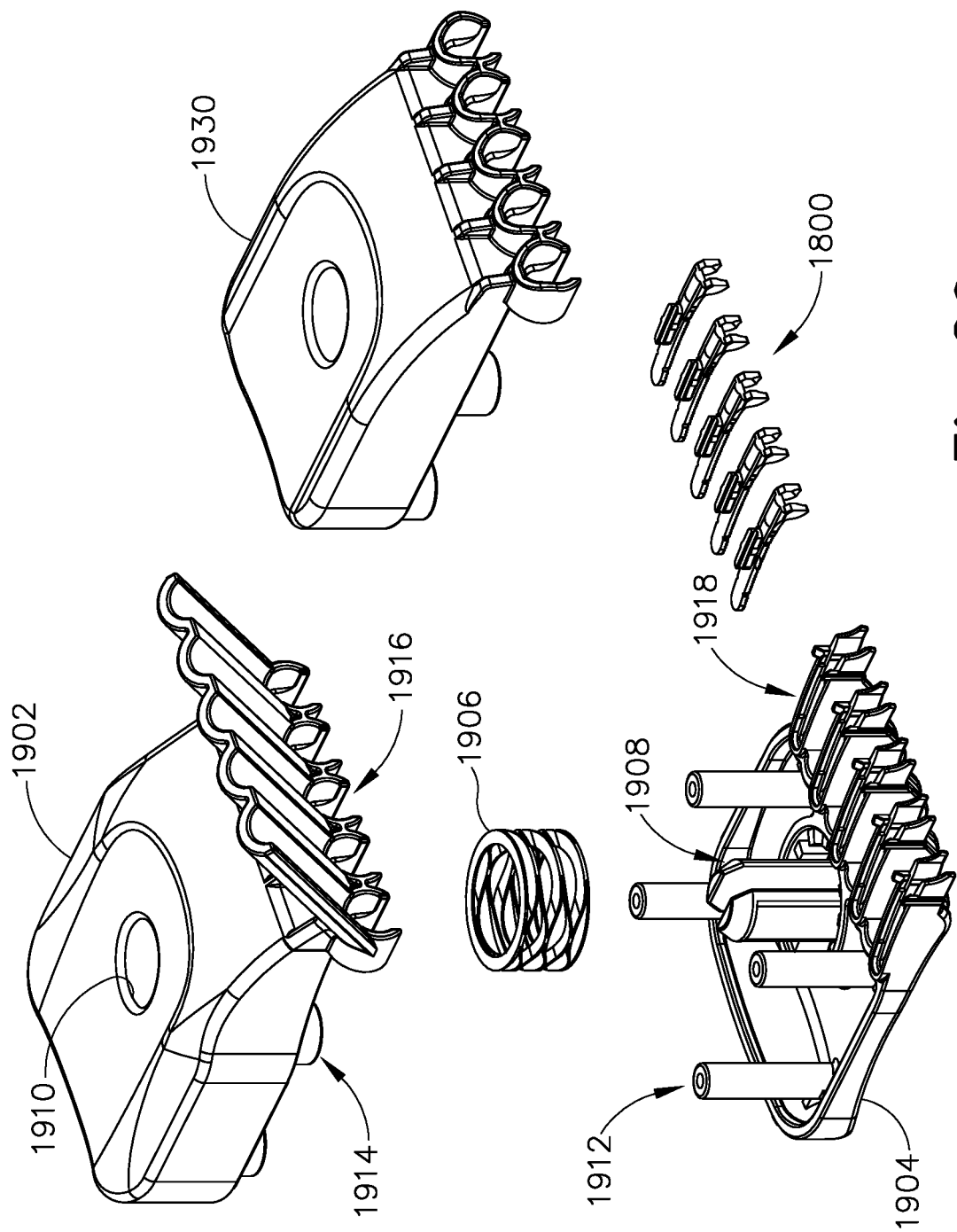
FIG. 29 depicts an exploded view of the clamp pad loader assembly of FIG. 27, shown with an alternate clamp arm guide lacking tube support that can be interchanged with the clamp arm guide having tube support.
Figure 30:
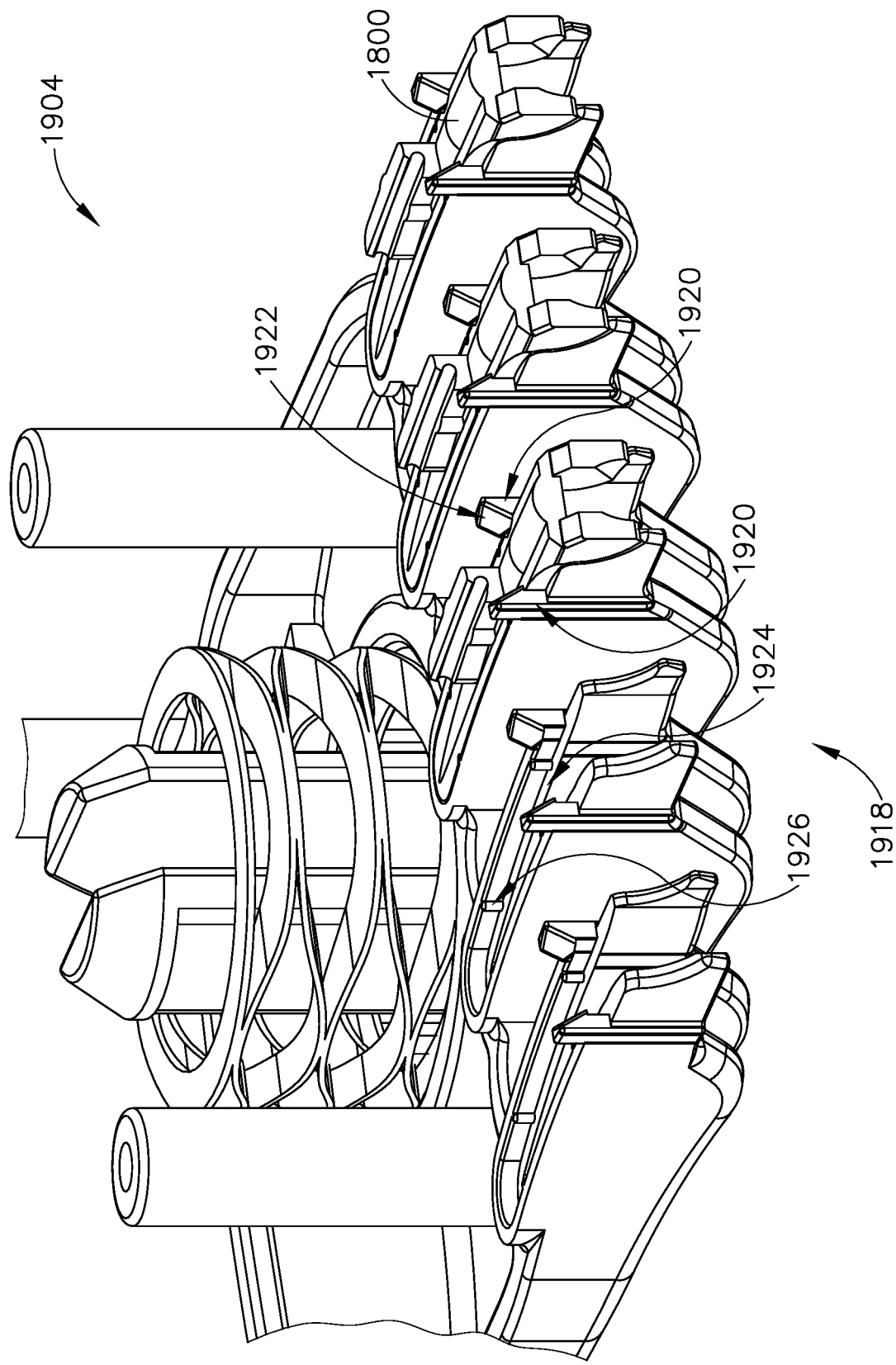
FIG. 30 depicts a partial perspective view of the clamp pad loader assembly of FIG. 27, showing a cartridge containing clamp pads for loading onto the clamp arm.

FIGS. 27-30 show an exemplary clamp pad loader assembly (1900) that may be used to install a new clamp pad (1800) into clamp arm (1570). Clamp pad loader assembly (1900) comprises a clamp arm guide (1902), a pad cartridge (1904), a wave spring assembly (1906), and a plurality of clamp pads (1800). Pad cartridge (1904) comprises a split post (1908), with wave spring assembly (1906) being positioned about split post (1908) as shown in FIG. 30. Split post (1908) is configured to engage with a bore (1910) in clamp arm guide (1902). Pad cartridge (1904) further comprises a plurality of guide posts (1912) that are configured to be received within a plurality of cylinder members (1914) extending from clamp arm guide (1902) as shown in FIG. 28A. As shown in FIG. 28A, when at rest, wave spring assembly (1906) biases the spacing between clamp arm guide (1902) and pad cartridge (1904) such that clamp arm (1570) can be received within a select one of a plurality of openings (1916) in clamp arm guide (1902) without interfering with any clamp pad (1800) retained within a select one of a plurality of clamp pad retention members (1918) of pad cartridge (1904).

In use, clamp pad loader assembly (1900) is actuated by moving clamp arm guide (1902) and pad cartridge (1904) toward each other, thereby compressing wave spring assembly (1906). FIG. 28A shows clamp pad loader assembly (1900) at rest with wave spring assembly (1906) in an uncompressed state. FIG. 28B shows clamp pad loader assembly (1900) in an actuated state where wave spring assembly (1906) is compressed and clamp arm guide (1902) and pad cartridge (1904) moved toward each other. As seen from a comparison of FIGS. 28A and 28B, clamp arm (1570) is positionable through one of openings (1916) when clamp pad loader assembly (1900) is in the configuration shown in FIG. 28A. To load a new clamp pad (1800) onto clamp arm (1570), with clamp arm (1570) inserted through one of openings (1916), clamp pad loader assembly (1900) is actuated to the position shown in FIG. 28B. It should be understood that when using clamp pad loader assembly (1900) to install clamp pad (1800) on clamp arm (1570), any used clamp pad (1800) previously installed on clamp arm (1570) is removed prior to using clamp pad loader assembly (1900). By way of example only, a flat bladed instrument may be used to push clamp pad (1800) out of engagement with tension wire (1578). Various suitable ways in which clamp arm (1570) may be removed from clamp arm (1570) will be apparent to those of ordinary skill in the art in view of the teachings herein.

As shown in FIG. 30, pad cartridge (1904) comprises a plurality of clamp pad retention members (1918). In the present example, cartridge (1904) includes 5 clamp pad retention members (1918), although clamp pad loader assemblies in other versions may be configured with greater or fewer clamp pad retention members (1918). Each clamp pad retention member (1918) is configured to retain one clamp pad (1800). To this end, each clamp pad retention member (1918) comprise a pair of grasping arms (1920) that are configured to releasably hold clamp pad (1800), with one grasping arm (1920) contacting a corresponding longitudinal side of clamp pad (1800). Grasping arms (1920) each have a chamfer (1922) that provides a contacting surface for damp arm (1570) as will be discussed further below.

Still referring to FIG. 30, clamp pad retention members (1918) each include base (1924) that supports clamp pad (1800) from beneath. Additionally, clamp pad retention members (1918) include multiple studs (1926) that project inwardly from the sides of clamp pad retention members (1918). Studs (1926) are configured to engage with corresponding depressions (1812) of clamp pad (1800) and this engagement provides longitudinal alignment of clamp pad (1800) within clamp pad retention members (1918).

To replace clamp pad (1800) installed on clamp arm (1570), first an operator removes any existing clamp pad (1800) from clamp arm (1570). As noted above, to remove clamp pad (1800) the operator may use a tool or instrument to push clamp pad (1800) down and through opening (1579) of clamp arm (1570) such that pad (1800) is freed from its connection with tension wire (1578). When loading or installing a new clamp pad (1800) onto clamp arm (1570), clamp arm (1570) is moved to an open position so as to not damage blade (1560) when using clamp pad loader assembly (1900). Next clamp arm (1570) is inserted through one of openings (1916) in clamp arm guide (1902) such that clamp arm (1570) is positioned above a loaded clamp pad (1800) retained within pad cartridge (1904).

With clamp arm (1570) within clamp pad loader assembly (1900), clamp pad loader assembly is actuated to the position shown in FIG. 28B. This action makes clamp arm (1570) contact grasping arms (1920) and specifically chamfer (1922) of grasping arms (1920). This contact deflects grasping arms (1920) outwardly away from clamp pad (1800), such that grasping arms (1920) disengage and thereby release clamp pad (1800). At about the same or similar time, boss (1806) of clamp pad (1800) is received within opening (1579) of clamp arm (1570) with chamfer (1808) deflecting tension wire (1578) such that clamp pad (1800) can be fully seated within opening (1579), with tension wire (1578) located within groove (1802) of clamp pad (1800). With clamp pad (1800) now connected with clamp arm (1570), clamp arm (1570) is removed from clamp pad loader assembly (1900) by moving clamp arm (1570) away from pad cartridge (1904) along a plane defined by clamp pads (1800) positioned within pad cartridge (1904). Once clamp arm (1570) with installed clamp pad (1800) are removed from pad cartridge (1904), grasping arms (1920) resiliently return to the at rest position shown in FIG. 30.

As shown in FIG. 29, clamp arm guide (1902) is shown as including tube support section (1928). Tube support section (1928) provides support to outer tube (1.580) of first disposable sub-assembly (1502) when using clamp pad loader assembly (1900). In some versions, clamp arm guide (1902) may be replaced with an alternate clamp arm guide (1930), as shown in FIG. 29, not having a tube support section. Other modifications to clamp pad loader assembly (1900) will be apparent to those of ordinary skill in the art in view of the teachings herein.

III. Exemplary Tray for Simple Life Cycle Determination

In some instances, a disposable sub-assembly designed to have multiple uses may be configured to stop operating after a predetermined amount of re-uses. Therefore, after a predetermined amount of re-uses is counted by a disposable sub-assembly, that sub-assembly may no longer work to form a complete surgical instrument. In such instances, it may be desirable to determine how many uses remain for a specific disposable sub-assembly that is configured to be cleaned, sterilized and re-used. This may allow an operator to discard a completely used disposable sub-assembly without accidentally cleaning, sterilizing, and attempting to reuse disposable sub-assembly.

Figure 31:
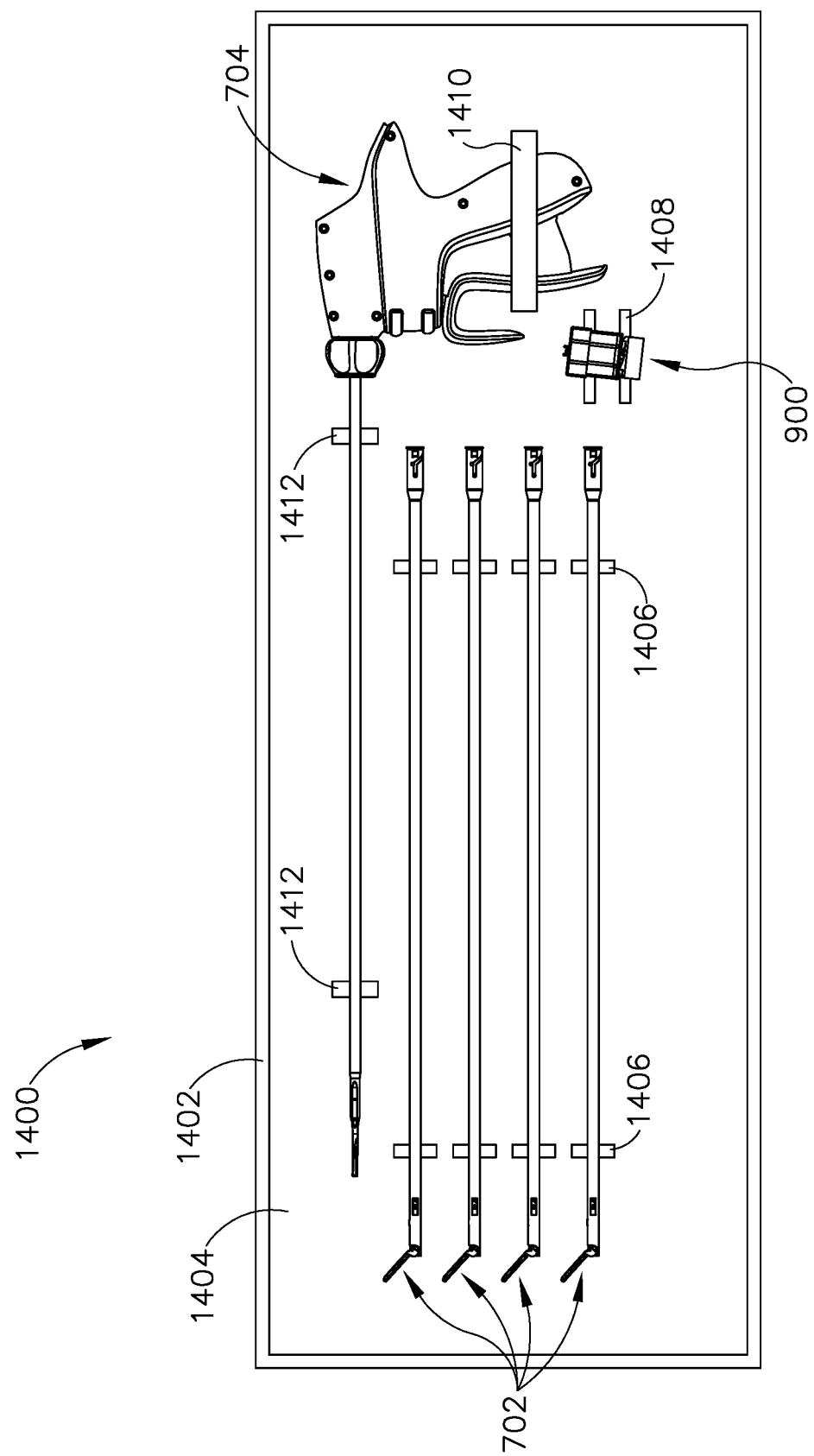
FIG. 31 depicts top plan view of a multi-use disposable assembly kit.

FIG. 31 shows a disposable assembly kit (1400) that may be used to determine the remaining uses for second disposable sub-assembly (704). Disposable assembly kit (1400) includes walls (1402) surrounded around a tray (1404), four first disposable sub-assemblies (702) removably attached to tray (1404) via snap fittings (1406), assembly tool (900) removably attached to tray via snap fittings (1408), and second disposable sub-assembly (704) removably attached to tray (1404) via snap fittings (1410, 1412). While in the current example, snap fittings (1406, 1408, 1410, 1412) are used to removably attach items to tray (1404) it should be understood that any other suitable means may be used to make items removably attached to tray as would be apparent to one having ordinary skill in the art in view of the teachings herein. While the current example shows tray (1404) storing disposable assembly (700), it should be understood tray (1404) may store disposable assembly (500, 1000, 1500) or any other disposable assembly as would be apparent to one having ordinary skill in the art in view of the teachings herein.

As mentioned above, tray (1404) stores four first disposable sub-assemblies (702). An operator may couple one first disposable sub-assembly (702) to second disposable sub-assembly (704), use disposable assembly (700) in a surgical procedure, decouple first disposable sub-assembly (702) from second disposable sub-assembly (704), discard first disposable sub-assembly, clean and sterilize second disposable sub-assembly (704), and return second disposable sub-assembly (704) to tray (1404). An operator may repeat this process until there are no longer any first disposable sub-assemblies (702) associated with tray (1404). This may indicate to an operator that second disposable sub-assembly (704) has no more remaining uses and should also be discarded.

Therefore, tray (1404) provides a means for storing, transporting, and tracking the number of reloads an operator has left.

While in the current example, four first disposable sub-assemblies (702) are used, it should be understood any suitable number of first disposable sub-assemblies (702) may be used as would be apparent to one having ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a reusable assembly comprising an ultrasonic transducer; (b) a first disposable sub-assembly comprising a clamp arm; (c) a second disposable sub-assembly comprising: (i) a pivotable trigger, and (ii) an ultrasonic waveguide, wherein the second disposable sub-assembly is configured to removably coupled with the reusable assembly; wherein the first disposable sub-assembly is configured to removably coupled with the second disposable sub-assembly, wherein the pivotable trigger is configured to rotate the clamp arm relative to the ultrasonic waveguide when the first disposable sub-assembly is coupled to the second disposable sub-assembly.

Example 2

The surgical instrument of Example 1, wherein the first disposable sub-assembly comprises a first inner tube and a first outer tube, wherein the first outer tube is pivotally coupled to the clamp arm, wherein the first inner tube is pivotally coupled to the clamp arm.

Example 3

The surgical instrument of Example 2, wherein the second disposable sub-assembly comprises a second inner tube having a proximal end and a distal end, wherein the second inner tube is configured to removably couple with the first inner tube at the distal end of the second inner tube.

Example 4

The surgical instrument of any one or more of Example 2 through 3, wherein the second disposable assembly comprises a knob member configured to rotate the ultrasonic waveguide about a longitudinal axis defined by the ultrasonic waveguide, wherein knob member houses a tube actuator, wherein the first outer tube is removable coupled to the tube actuator.

Example 5

The surgical instrument of Example 4, wherein the knob member defines a keyway and a rotation path, wherein the keyway and rotation path are configured to align the first disposable sub-assembly when coupled to the second sub-assembly.

Example 6

The surgical instrument of any one or more of Examples 1 through 5, wherein the second disposable sub-assembly has a counting mechanism to determine how many times the second disposable sub-assembly has been used.

Example 7

An assembly tool for use with any of the surgical instruments of Examples 1 through 6, where the assembly tool comprises a torque wrench configured to properly couple the reusable assembly with the second sub-assembly.

Example 8

The assembly tool of Example 7, wherein the assembly tool also comprises a spanner wrench configured to rotate the first sub-assembly relative to the second sub-assembly.

Example 9

The assembly tool of Example 7, wherein the assembly tool is configured to fix the first sub-assembly relative to the assembly tool.

Example 10

The assembly tool of Example 9, wherein the assembly tool comprises a base member and a top member, wherein the top member is configured to pivot relative to the base member from an open position to a closed position, wherein the assembly tool is configured to fix the first sub-assembly relative to the assembly tool when the top member is in the closed position.

Example 11

The assembly tool of Example 10, wherein the assembly tool is configured to selectively lock when the top member is in the closed position Example 12

The assembly tool of any one or more of Examples 9 through 11, wherein the assembly tool further has a locator feature configured to fix the first disposable sub-assembly in the same position relative to the assembly tool.

Example 13

The assembly tool of Example 12, wherein the locator feature comprises a locator pin.

Example 14

The assembly tool of Example 13, wherein the locator pin is biased to a first position, wherein the locator pin is configured to translate from the first position to the a second position in response to the top member pivoting from the open position to the closed position.

Example 15

The assembly tool of any one or more of Example 9 through 14, wherein the first inner tube comprises a first alignment hole, wherein the first outer tube each comprises a second alignment hole, wherein the locator pin is configured to insert through the first alignment hole and the second alignment hole.

Example 16

The assembly tool of Example 15, wherein the locator pin and the first inner tube define a gap configured to receive the ultrasonic waveguide when the locator pin is in the second position.

Example 17

The assembly tool of any one or more of Example 9 through 16, wherein the assembly tool comprises a tubular surface configured to conform to at least a portion of first outer tube.

Example 18

The assembly tool of any one or more of Example 9 through 16, wherein the assembly tool is pivotable via a living hinge.

Example 19

The surgical instrument of Example 6, wherein the second disposable sub-assembly further comprises an indicator, wherein the indicator is configured to show whether the second disposable sub-assembly has been used a predetermined number of times.

Example 20

The surgical instrument of Example 19, wherein the indicator is activated by a button.

Example 21

An apparatus, comprising: (a) a body; (b) a shaft assembly, wherein the shaft assembly comprises: (i) an outer tube, (ii) an inner tube, and (iii) an acoustic waveguide; and (c) an end effector, wherein the end effector comprises: (i) an ultrasonic blade acoustically coupled with the acoustic waveguide, and (ii) a clamp arm, wherein a first portion of the clamp arm is pivotably coupled with a distal end of the outer tube, wherein a second portion of the clamp arm is pivotably coupled with a distal end of the inner tube; wherein the outer tube and the inner tube are configured to removably couple with the body such that the outer tube, the inner tube, and the clamp arm are configured to removably couple with the body and the remainder of the shaft assembly and end effector as a unit.

Example 22

The apparatus of Example 21, wherein the outer tube proximally terminates in a proximal end, wherein the inner tube proximally terminates in a proximal end, wherein the proximal end of the inner tube is proximal to the proximal end of the outer tube.

Example 23

The apparatus of any one or more of Examples 21 through 22, wherein the outer tube is configured to translate relative to the body and relative to the inner tube while the inner tube remains stationary relative to the body.

Example 24

The apparatus of any one or more of Examples 21 through 23, wherein the inner tube proximally terminates in a proximal end, wherein the proximal end of the inner tube defines a guide slot, wherein the body includes a guide feature configured to fit in the guide slot, wherein the guide feature and the guide slot are configured to cooperate with each other to thereby govern angular positioning of the inner tube relative to the acoustic waveguide.

Example 25

The apparatus of Example 24, wherein the guide slot comprises a first portion and a second portion, wherein the first portion is oriented parallel to a longitudinal axis of the shaft assembly, wherein the second portion is non-parallel with the longitudinal axis of the shaft assembly.

Example 26

The apparatus of any one or more of Examples 21 through 25, wherein the body includes a latch, wherein the latch is configured to cooperate with the outer tube to thereby secure longitudinal positioning of the outer tube relative to the body.

Example 27

The apparatus of Example 26, wherein the body comprises: (i) a housing, and (ii) a knob member, wherein the knob member is operable to rotate the shaft assembly relative to the housing.

Example 28

The apparatus of Example 27, wherein the knob member includes a cantilevered button, wherein the cantilevered button is operable to disengage the latch from the outer tube.

Example 29

The apparatus of any one or more of Examples 26 through 28, wherein the outer tube proximally terminates at a proximal end, wherein the proximal end has a lateral opening, wherein the latch is configured to cooperate with the lateral opening to thereby secure longitudinal positioning of the outer tube relative to the body.

Example 30

The apparatus of Example 29, wherein the latch comprises a prong, wherein the lateral opening is configured to receive the prong.

Example 31

The apparatus of any one or more of Examples 21 through 30, wherein the outer tube includes a laterally oriented flush port, wherein the flush port is in fluid communication with a space defined between the inner tube and the outer tube.

Example 32

The apparatus of any one or more of Examples 21 through 31, wherein the clamp arm comprises a clamp arm body and a clamp pad, wherein the clamp arm body is configured to removably receive the clamp pad.

Example 33

The apparatus of Example 32, wherein the clamp arm body defines an opening, wherein the clamp arm further comprises a tension wire extending through the opening, wherein the tension wire is configured to removably retain the clamp pad relative to the clamp arm body.

Example 34

The apparatus of Example 33, wherein the clamp pad includes a boss defining a groove, wherein the groove is configured to receive the tension wire.

Example 35

The apparatus of Example 34, wherein the boss further comprises a chamfer, wherein the chamfer is configured to deflect the tension wire as the clamp pad is secured to the clamp arm body.

Example 36

An apparatus, comprising: (a) a body; (b) a shaft assembly, wherein the shaft assembly comprises: (i) an outer tube, (ii) an inner tube, and (iii) an acoustic waveguide; and (c) an end effector, wherein the end effector comprises: (i) an ultrasonic blade acoustically coupled with the acoustic waveguide, and (ii) a clamp arm, comprising: (A) a clamp arm body, wherein a first portion of the clamp arm body is pivotably coupled with a distal end of the outer tube, wherein a second portion of the clamp arm body is pivotably coupled with a distal end of the inner tube, wherein the clamp arm body defines an opening, (B) a tension wire extending through the opening, and (C) a clamp pad, wherein the tension wire is configured to removably secure the clamp pad to the clamp arm body.

Example 37

The apparatus of Example 36, further comprising a clamp pad loader assembly, wherein the clamp pad loader assembly is configured to receive the clamp arm body, wherein the clamp pad loader assembly is further configured to removably retain at least one clamp pad, wherein the damp pad loader assembly is further configured to load the retained at least one clamp pad onto the clamp arm body.

Example 38

The apparatus of Example 37, wherein the clamp pad loader assembly further comprises: (i) a body, (ii) a latch, wherein the latch is configured to removably secure the at least one clamp pad to the body, and (iii) an actuator, wherein the actuator is configured to disengage the latch to thereby release the at least one clamp pad from the body of the clamp pad loader.

Example 39

A method of assembling an instrument, the method comprising: (a) grasping an instrument body, wherein an acoustic waveguide extends distally from the instrument body, wherein the acoustic waveguide has a distal end including an ultrasonic blade; (b) grasping a shaft assembly, wherein the shaft assembly comprises: (i) an inner tube, wherein the inner tube distally terminates in a distal end, wherein the inner tube proximally terminates in a proximal end, (ii) an outer tube, wherein the outer tube distally terminates in a distal end, wherein the outer tube proximally terminates in a proximal end, and (iii) a clamp arm, wherein the clamp arm is pivotably coupled with the distal end of the inner tube, wherein the clamp arm is further pivotably coupled with the distal end of the outer tube; (c) inserting the proximal ends of the inner and outer tubes into the instrument body, wherein the proximal ends of the inner and outer tubes are inserted into the instrument body as a unit; (d) securing the proximal ends of the inner and outer tubes in the instrument body, wherein the clamp arm and the ultrasonic blade cooperate to define an end effector after the proximal ends of the inner and outer tubes are secured in the instrument body.

Example 40

The method of Example 39, further comprising pressing a clamp pad into engagement with a clamp arm body to thereby form the clamp arm, wherein the act of pressing a clamp pad into engagement with a clamp arm body comprises deflecting a resilient feature secured to the clamp arm body.

V. Miscellaneous

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071; U.S. Pub. No. 2011/0015660, issued as U.S. Pat. No. 8,461,744 on Jun. 11, 2013; U.S. Pub. No. 2012/0112687, issued as U.S. Pat. No. 9,381,058; U.S. Pub. No. 2012/0116265, now abandoned; U.S. Pub. No. 2014/0005701, issued as U.S. Pat. No. 9,393,037; U.S. Pub. No. 2015/0080924, issued as U.S. Pat. No. 10,172,636; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A clamp pad loader assembly, comprising:
   (a) a clamp arm guide defining a plurality of openings, wherein each of the plurality of openings is dimensioned to receive a clamp arm of an ultrasonic instrument;
   (b) a clamp pad cartridge coupled with the clamp arm guide, wherein the clamp pad cartridge comprises:
      (i) a plurality of clamp pad retention members respectively aligned with the plurality of openings, wherein the plurality of clamp pad retention members includes a first clamp pad retention member, and
      (ii) a clamp pad housed within the first clamp pad retention member of the plurality of clamp pad retention members, wherein the clamp pad cartridge and the clamp arm guide are configured to actuate relative to each other between an open position and a closed position while the clamp arm of the ultrasonic instrument is within a first opening of the plurality of openings in order to couple the clamp arm with the first clamp pad housed within the first clamp pad retention member of the plurality of clamp pad retention members; and
   (c) a biasing member disposed between the clamp arm guide and the clamp pad cartridge, wherein the biasing member biases the clamp arm guide and the clamp pad cartridge toward the open position.

2. The clamp pad loader assembly of claim 1, wherein the biasing member comprises a wave spring.

3. The clamp pad loader assembly of claim 2, wherein the clamp pad cartridge comprises a split post, and wherein the wave spring is disposed on the split post.

4. The clamp pad loader assembly of claim 3, wherein the clamp arm guide defines a bore, and wherein the split post extends within the bore.

5. The clamp pad loader assembly of claim 1, wherein the clamp pad cartridge comprises a plurality of guide posts, and wherein the clamp arm guide comprises a plurality of cylindrical members dimensioned to slidably receive the plurality of guide posts, respectively.

6. The clamp pad loader assembly of claim 1, wherein the clamp arm guide comprises a plurality of tube support sections extending respectively from the plurality of openings, and wherein the plurality of tube support sections are configured to support a shaft assembly of the ultrasonic instrument.

7. The clamp pad loader assembly of claim 1, wherein the first clamp pad retention member of the plurality of clamp pad retention members comprises a pair of grasping arms configured to releasably hold the clamp pad.

8. The clamp pad loader assembly of claim 7, wherein each of the pair of grasping arms comprises a chamfered surface configured to release the clamp pad from the pair of grasping arms in response to the clamp pad cartridge and the clamp arm guide actuating relative to each other between the open position and the closed position while the clamp arm of the ultrasonic instrument is within the first opening of the plurality of openings.

9. The clamp pad loader assembly of claim 1, wherein the first clamp pad retention member of the plurality of clamp pad retention members comprises a plurality of studs configured to engage the clamp pad to thereby longitudinally align the clamp pad with the first clamp pad retention member.

10. The clamp pad loader assembly of claim 1, wherein the clamp pad comprises a boss configured to fit within the first opening of the clamp arm of the ultrasonic instrument.

11. The clamp pad loader assembly of claim 10, wherein the boss defines a first groove configured to receive a tension wire of the clamp arm of the ultrasonic instrument.

12. The clamp pad loader assembly of claim 11, wherein the boss comprises a chamfer configured to deflect the tension wire into engagement with the first groove as the clamp arm couples with the clamp pad.

13. The clamp pad loader assembly of claim 12, wherein the clamp pad comprise a pair of studs configured to engage with a pair of grooves defined by the clamp arm to thereby longitudinally align the clamp pad with the clamp arm, respectively.

14. The clamp pad loader assembly of claim 1, wherein the clamp pad comprises a polytetrafluoroethylene material.

15. A clamp pad loader assembly, comprising:
(a) a clamp arm guide defining a plurality of openings, wherein each of the plurality of openings is dimensioned to receive a clamp arm of an ultrasonic instrument;
(b) a clamp pad cartridge coupled with the clamp arm guide, wherein the clamp pad cartridge comprises a plurality of clamp pad retention members respectively aligned with the plurality of openings; and
(c) a plurality of clamp pads, wherein the plurality of clamp pads are respectively housed within the plurality of clamp pad retention members, wherein the clamp pad cartridge and the clamp arm guide are configured to actuate relative to each other between an open position and a closed position while the clamp arm of the ultrasonic instrument is within an opening of the plurality of openings in order to couple the clamp arm with the clamp pad respectively housed within the clamp pad retention member; and
(d) a biasing member disposed between the clamp arm guide and the clamp pad cartridge, wherein the biasing member biases the clamp arm guide and the clamp pad cartridge toward the open position.

16. The clamp pad loader assembly of claim 15, wherein the clamp arm guide defining the opening is configured to drive the clamp arm toward the clamp pad.

17. The clamp pad loader assembly of claim 15, wherein the clamp pad cartridge is slidably coupled with the clamp arm guide.

18. The clamp pad loader assembly of claim 15, wherein each of the plurality of clamp arm retention members comprises a base configured to support the clamp pad, respectively.

19. A clamp pad loader assembly, comprising:
(a) a clamp arm guide defining a first opening dimensioned to receive a clamp arm of an ultrasonic instrument;
(b) a clamp pad cartridge coupled with the clamp arm guide, wherein the clamp pad cartridge comprises a first clamp pad retention member aligned with the first opening;
(c) a first clamp pad housed within the first clamp pad retention member, wherein the clamp pad cartridge and the clamp arm guide are configured to actuate relative to each other between an open position and a closed position while the clamp arm of the ultrasonic instrument is within the first opening in order to couple the clamp arm with the first clamp pad housed within the first clamp pad retention member; and
(d) a biasing member disposed between the clamp arm guide and the clamp pad cartridge, wherein the biasing member biases the clamp arm guide and the clamp pad cartridge toward the open position.

20. The clamp pad loader assembly of claim 19, further comprising a second clamp pad retention member and a second clamp pad, wherein the clamp arm further defines a second opening, wherein the second clamp pad retention member is aligned with the second opening, and wherein the second clamp pad is housed within the second clamp pad retention member.

* * * * *